United States Patent
Chretien et al.

(10) Patent No.: US 9,499,792 B2
(45) Date of Patent: Nov. 22, 2016

(54) METHODS FOR OBTAINING STEM CELLS

(75) Inventors: Fabrice Chretien, Paris (FR); Mathilde Latil, Creteil (FR); Shahragim Tajbakhsh, Paris (FR)

(73) Assignees: CENTRE NATIONAL DE LARECHERCHE SCIENTIFIQUE (C.N.R.S), Paris (FR); INSTITUT PASTEUR, Paris (FR)

( * ) Notice: Subject to any disclaimer, the term of this patent is extended or adjusted under 35 U.S.C. 154(b) by 0 days.

(21) Appl. No.: 13/700,832

(22) PCT Filed: Jun. 3, 2011

(86) PCT No.: PCT/EP2011/059214
§ 371 (c)(1),
(2), (4) Date: Feb. 27, 2013

(87) PCT Pub. No.: WO2011/151452
PCT Pub. Date: Dec. 8, 2011

(65) Prior Publication Data
US 2013/0149286 A1 Jun. 13, 2013

(30) Foreign Application Priority Data
Jun. 4, 2010 (EP) .................................... 10305603

(51) Int. Cl.
*A61K 35/28* (2015.01)
*C12N 5/0797* (2010.01)
*C12N 5/071* (2010.01)
*C12N 5/0789* (2010.01)
*C12N 5/0775* (2010.01)
*C12N 5/077* (2010.01)
*A01N 1/02* (2006.01)

(52) U.S. Cl.
CPC ............ *C12N 5/0668* (2013.01); *A01N 1/021* (2013.01); *A01N 1/0284* (2013.01); *A61K 35/28* (2013.01); *C12N 5/0623* (2013.01); *C12N 5/0647* (2013.01); *C12N 5/0659* (2013.01)

(58) Field of Classification Search
None
See application file for complete search history.

(56) References Cited

U.S. PATENT DOCUMENTS

2009/0053182 A1* 2/2009 Ichim et al. ................. 424/93.7

FOREIGN PATENT DOCUMENTS

WO WO 01/53462 A1 7/2001

OTHER PUBLICATIONS

Stachelscheid, Harald; et al; "Isolation and Characterization of Adult Human Liver Progenitors from Ischemic Liver Tissue Derived from Therapeutic Hepatectomies" Tissue Engineering: Part A, 15, 1633-1643, 2009.*
Ivanovic, Zoran; "Hypoxia or In Situ Normoxia: The Stem Cell Paradigm" Journal of Cellular Physiology, 219, 271-275, 2009.*
International Search Report for corresponding International Application No. PCT/EP2011/059214, dated Oct. 31, 2011.
Moshkin, S.A., et al., "Formation Dynamics of fibroblast-like cells in the monolayer culture of cadaveric post mortem bone marrow," Probl Gematol Pereliv Krovi., 1976, vol. 21, No. 5, pp. 39-42. Abstract.
Liu, P. I., et al., "Proliferative function of cadaveric bone marrow cells." Am J Hematol. 1978; vol. 5, No. 2: pp. 145-50.
Söderdahl, G., et al., "Cadaveric bone marrow and spleen cells for transplantation," Bone Marrow Transplant. Jan. 1998; vol. 21, No. 1: pp. 79-84.
Marlicz W., et al., "Isolation of hematopoietic stem cells from heparinized cadaveric multiple organ donors: Potential clinical implications," Transplantation Proceedings. vol. 31. No. 5. Aug. 1999, pp. 2099-2101.
D'Ippolito, G., et al., "Marrow-isolated adult multilineage inducible (MIAMI) cells. a unique population of postnatal young and old human cells with extensive expansion and differentiation potential." Journal of Cell Science. vol. 117., Part 14, Jun. 2004. pp. 2971-2981.
Ahrens, Norbert et al., "Mesenchymal stem cell content of human vertebral bone marrow" Transplantation. Williams and Wilkins. Baltimore US. vol. 78. No. 6. Sep. 27, 2004. pp. 925-929.
Erker, L., et al., "Therapeutic liver reconstitution with murine cells isolated long after death." Gastroenterology. vol. 139, No. 3. Jun. 2, 2010, pp. 1019-1029.
Tetsuro, Tamaki, et al., "Skeletal muscle-derived CD34+/45− and CD34−/45− stem cells are situated hierarchically upstream of Pax7+ cells." Stem Cells and Development. vol. 17. No. 4. Aug. 1, 2008, pp. 653-668.
P. S. Zammit et al., "The skeletal muscle satellite cell: the stem cell that came in from the cold." Journal of Histochemistry & Cytochemistry. vol. 54. No. 11. Jul. 24, 2006, pp. 1177-1191.
Legrand, F., et al., "Endothelial cells within embryonic skeletal muscles: a potential source of myogenic progenitors." Experimental Cell Research. Academic Press. US. vol. 301. No. 2., Dec. 10, 2004. pp. 232-241.
Olguin, H. C., et al., "Pax-7 up-regulation inhibits myogenesis and cell cycle progression in satellite cells: a potential mechanism for self-renewal." Developmental Biology. Academic Press. New York. NY. US. vol. 275. No. 2., Nov. 15, 2004. pp. 375-388.
Lonergan, et al., "Mitochondria in stem cells" Mitochondrion. Elsevier. Amsterdam. NL. vol. 7. No. 5. Aug. 28, 2007 pp. 289-296.
Duguez, Stephanie, et al., "Mitochondrial biogenesis during skeletal muscle regeneration". American Journal of Physiology. vol. 282. No. 4 Part 1. Apr. 2002. pp. E802-E809.
Tanaelle Dupas et al., "Fetal muscle contains different CD34+ cell subsets that distinctly differentiate into adipogenic, angiogenic and myogenic lineages." Stem Cell Res. Jul. 2, 2011. pp. 230-243.

* cited by examiner

*Primary Examiner* — Renee Claytor
*Assistant Examiner* — David Berke-Schlessel
(74) *Attorney, Agent, or Firm* — Davidson, Davidson & Kappel LLC

(57) ABSTRACT

The present invention relates to methods for obtaining stem cells from mammalian cadavers, methods for obtaining or purifying stem cells from a sample likely to contain non-stem cells, methods of regeneration of injured tissues and methods of treatment.

13 Claims, 8 Drawing Sheets

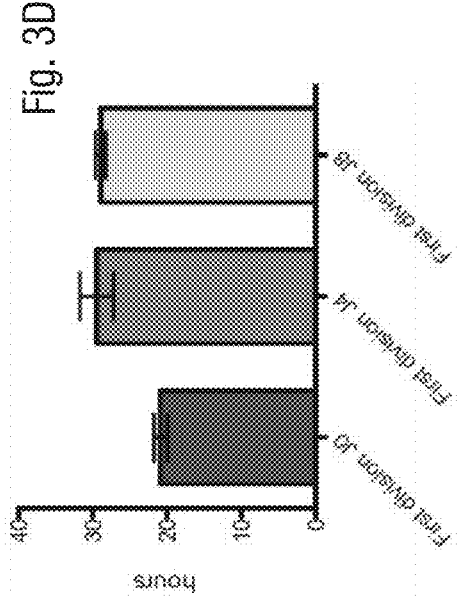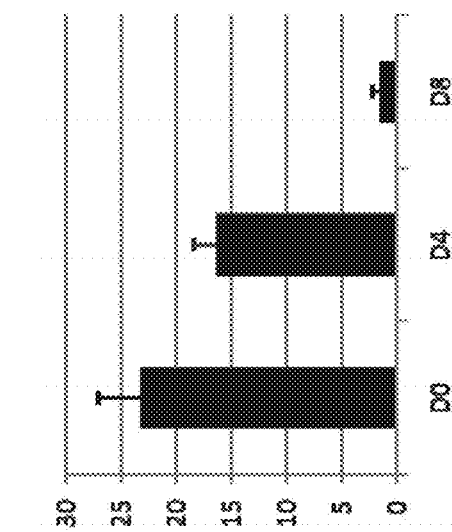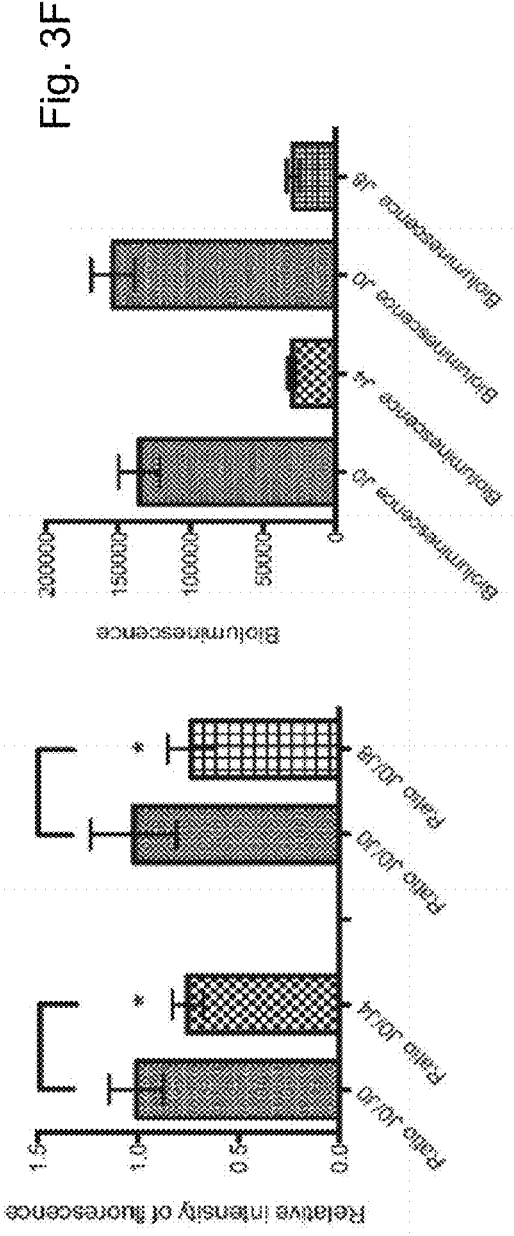

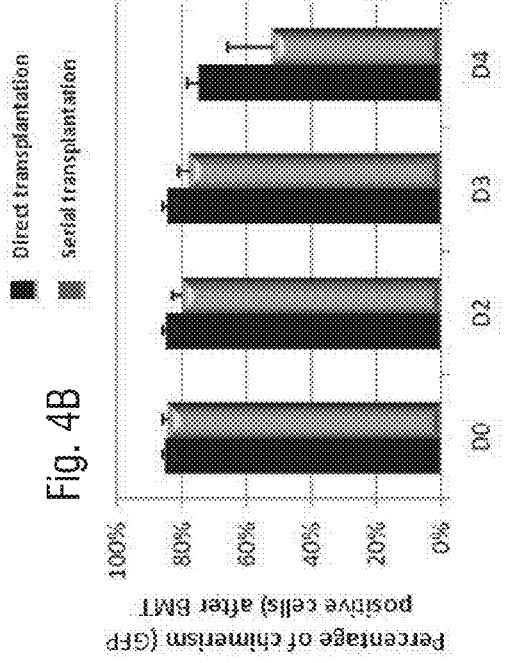
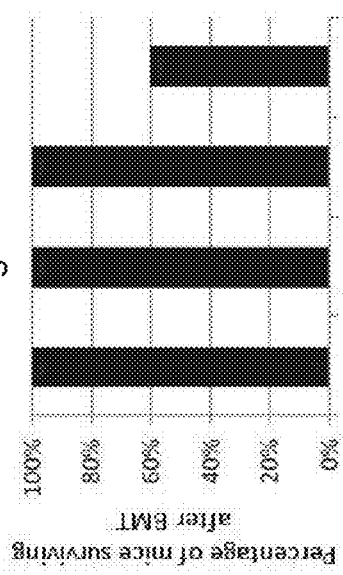
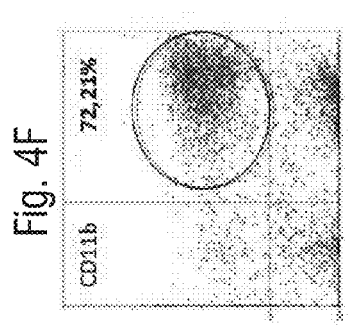
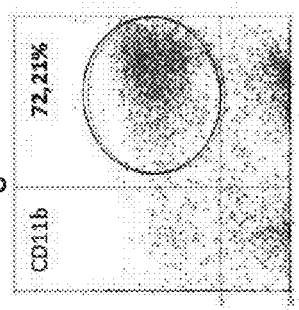
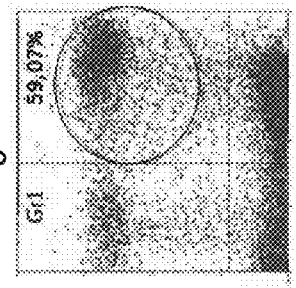
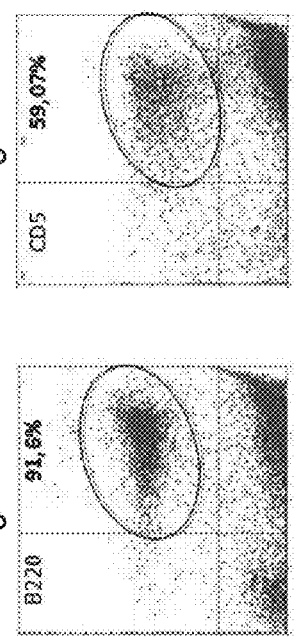

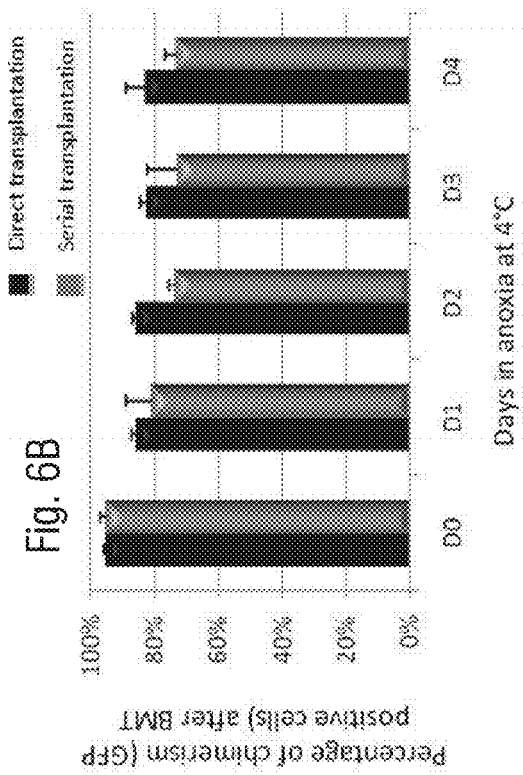
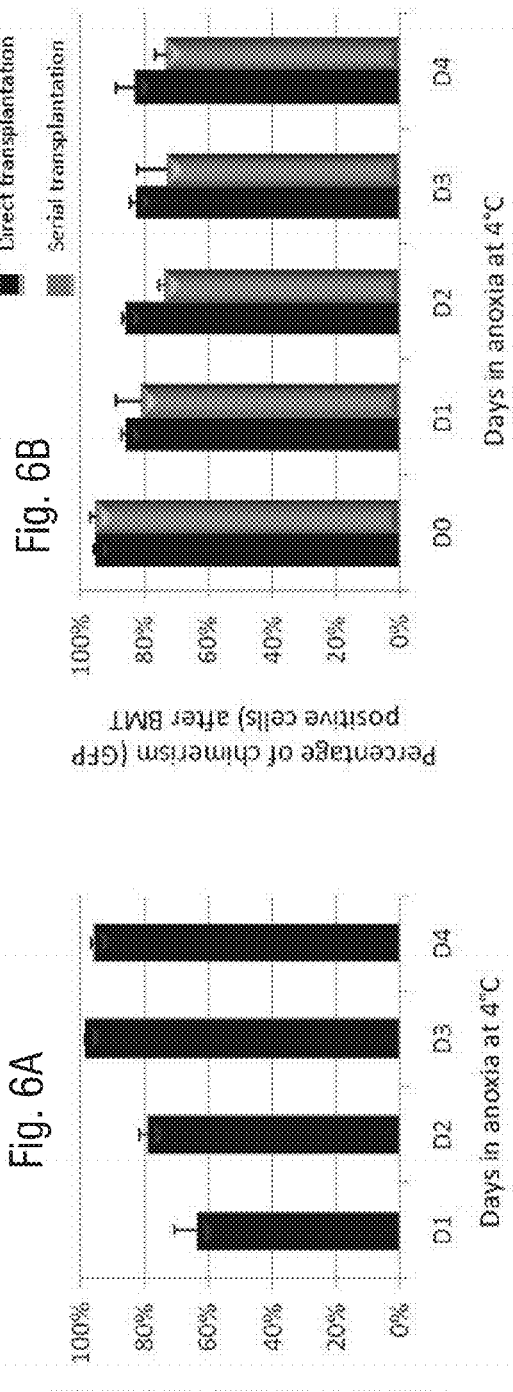
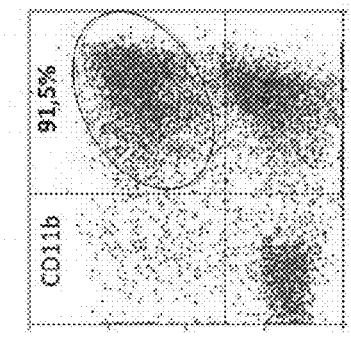
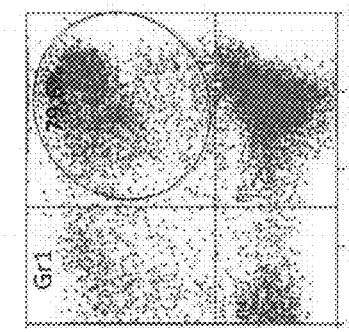
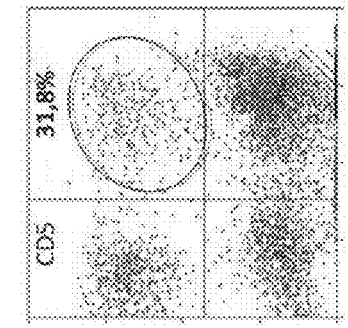
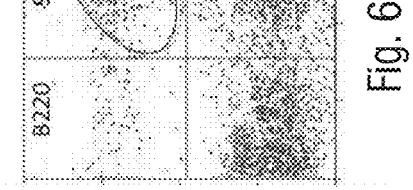

METHODS FOR OBTAINING STEM CELLS

This application is a U.S. national phase application of International Application No. PCT/EP2011/059214, filed Jun. 3, 2011, which claims priority to European Patent Application No. 10305603.2, filed Jun. 4, 2010, the disclosures of which are all hereby incorporated by reference herein.

FIELD OF THE INVENTION

The present invention relates to methods for obtaining stem cells from mammalian cadavers, methods for obtaining or purifying stem cells from a sample likely to contain non-stem cells, methods of regeneration of injured tissues and methods of treatment.

BACKGROUND OF THE INVENTION

There is strong clinical and scientific interest in finding new sources of stem cells which are readily available, since stem cells have a great importance for biological studies, stem cells therapies and regenerative medicine.

Two main types of mammalian stem cells exist: embryonic stem cells (hereinafter abbreviated "eSC") and "adult" or "somatic" stem cells (hereinafter abbreviated "sSC").

The former type was isolated from human embryos more than one decade ago (Thomson et al., Science, 282(5891): 1145-1147, 1998). Thomson et al. discovered a method to derive and isolate these cells from embryos and foetal germ cells. eSC have the potential to develop into almost all of the more than 200 different known human body cells.

The second type of known stem cells is undifferentiated cells that are found in differentiated somatic tissue. Generally these cells are multipotent, i.e. having the capacity to differentiate into several types of somatic cell within the tissue in which they reside.

During the last ten years, sSC have been found in many organs and tissues, including central nervous system, bone marrow, peripheral blood, blood vessels, umbilical cordon blood, skeletal muscle, epidermis of the skin, dental pulp, heart, gut, liver, pancreas, lung, adipose tissue, ovarian epithelium, retina, cornea and testis. They are thought to reside in a specific area of each tissue, which is called a "stem cell niche".

In vivo, the main role of sSC is to maintain homeostasis and to replace cells that have died because of use, apoptosis, injury or disease. However, most sSC have a limited capacity to handle major trauma or diseases that would cause a vast loss of cells and tissue.

Both types of stem cells have the ability to proliferate while maintaining an undifferentiated state and the capacity to give rise to a succession of mature functional differentiated cells.

However, whereas eSC are pluripotent, i.e. they can differentiate into almost all cell types of the body and possess the capability of developing into any organ or tissue type, sSc are multipotent, which means that sSC can only differentiate into several types of cell which are closely related to the tissue from which sSC derive. For example, a hematopoietic stem cell may only give rise to any of the different types of terminally differentiated blood cells.

Even if the embryonic stem cells have the greatest degree of differentiation potential, they are not readily available and procurement of these cells from embryos or foetal tissue, including abortuses, raises religious and ethical issues.

On the contrary, several types of sSC such as mesenchymal stem cells, hematopoietic stem cells, skin stem cells, adipose-derived stromal stem cells, are more accessible and provoke less ethical controversy than eSC. Further, in some cases stem cells can be obtained from the patient to be engrafted, i.e. the recipient which is better suitable for transplantation purpose than eSC since autologous graft avoids the risk of rejection.

Unfortunately, sCS are rare and present in small quantity in somatic tissues. Since very few stem cells are present in adult tissues, extraction procedures to recover these cells from a tissue generally result in contamination by other cell types such as fibroblasts. Consequently, when a tissue sample is harvested, it is necessary to sort a heterogeneous mixture comprising stem cells and non-stem cells. However, a specific cellular marker characterising one type of sSC does not always exist, making it difficult to isolate sSC from other cell-types of the sample. Hence, to date, isolation of normally occurring populations of stem cells from adult tissues is technically difficult and costly.

Moreover, even if sCS are more readily available than eSC, a major issue which remains to be solved is the acute organ and bone marrow shortage mainly due to the small number of donors, and which is increased by the difficulty to find matching donors, especially for minority groups.

Accordingly, there is a need for a new source of readily available stem cells. Furthermore, there is also a great need for a simple method which enables for specifically selecting any type of stem cell from biological material comprising non-stem cells.

Recently, it has been shown that neural stem cells from rat can be isolated from the brain of deceased adult or early postnatal rats even 6 days after death when rats were stored at 4° C. (Yi Xu et al., Journal of Neuroscience Research, 74: 533-540, 2003). Then, Yi Xu et al. suggested using cadavers as a new source of neural stem cells usable for clinical purposes. Further, the study of Yi Xu et al. showed that the amount of stem cells obtained from rat cadavers depends on the age of the rats, since there are significantly more neural stem cells in the early postnatal rats than in the adults. In addition, Yi Xu et al. showed that from day 2 post-mortem the number of neural stem cells strongly decreases and that only few neural stem cells survive 4 days after death in 4 weeks old rats.

A recent study performed on human neural stem cells indicates that the highest proliferation rate is obtained when these cells are cultured in hypoxic conditions, at an oxygen concentration between 2.5 and 5%, while 1% of oxygen is detrimental for cell survival (Santilli et al., PLOS One, 5(1): e8575, 2010). This study suggests that an oxygen concentration of less that 2.5% is noxious for stem cells.

Another study conducted on human abortuses preserved at 4° C. clearly showed that the number of viable neural stem cells decreased sharply when preservation is prolonged to 12 hours after death (Xinchun Liu and al., Journal of Neuroscience methods, 157: 64-70, 2006). Viable neural progenitor cells from human cadavers were also obtained from brain tissue 20 hours after death (Palmer et al., Nature, 411: 42-43, 2001).

It was also proposed in the International Application WO 01/53462 to use tissues of cadavers as a source of progenitors and stem cells, in particular as a source of progenitor cells having the capacity to develop into hepatocytes and biliary cells. WO 01/53462 recommended to use tissues which had been harvested within about six hours after the donor's heartbeat ceased, and a maximum of 30 hours post-mortem was indicated for liver tissue. However, it is to be noted that this application showed experiments only for liver progenitor cells which come from livers obtained not later than 30 hours after death.

It was also shown that the cell viability of adult rat neural stem cells when cultured 24 hours in anoxic condition at 37° C. increased up to 60% compared to normoxic condition (Bürgers et al., Exp. Brain Res., 188(1): 33-43, 2008), and that cell division activity increased from 2% in normoxic condition to 16% in anoxic condition. However, the effect of longer periods in anoxia on viability of stem cells was not tested and the transplantation potential of stem cells was not assessed.

Concerning neural stem cells, histological and immuno-histochemical assays suggest that the rich vascular bed presents in brain, in particular the subventricular zone, might be an important element responsible for survival of neural stem cells during the post-mortem period and can likely act as a niche for the maintenance of neural stem cells (Yi Xu et al., Journal of Neuroscience Research, 74: 533-540, 2003).

As indicated above, the prior art mainly concerns neural stem cells and does not demonstrate that other type of stem cells can be obtained from cadavers, except liver stem cells. Further, the longest period of time following death after which viable stem cells could be found was 6 days for rat neural stem cells. Viability of human neural stem cells was assessed only until 20 hours post mortem.

In addition, because the biological environment of neural stem cells is specific and not found in other tissues, data of the prior art relating to neural stem cells do not allow to conclude that other types of stem cells can be obtained from cadavers.

SUMMARY OF THE INVENTION

Unexpectedly, the inventors have observed that stem cells, in particular human skeletal muscle stem cells and hematopoietic stem cells, have the capacity to resist in the absence of oxygen for a period of time longer than the periods of time previously reported in the art. In particular, the inventors have shown that stem cells from human cadavers can resist for up to 17 days after death, and resist better than non-stem cells to deprivation of oxygen.

They also shown, firstly that mouse skeletal muscle stem cells can survive at least 10 days after death and can reform muscle in vitro, and secondly that bone marrow harvested at least until 4 days after death can be efficiently transplanted and eventually serially transplanted in irradiated mice to reconstitute bone marrow, demonstrating that the stem cells even long term repopulating stem cells are viable and functional in vivo.

These results indicate that cadavers, even several days after death, are an important source of stem cells, in particular of muscle stem cells (especially muscle stem cells obtained from skeletal muscle or smooth muscle) and hematopoietic stem cells, useful for stem cells therapies and regenerative medicine.

Method for Obtaining Stem Cells from a Cadaver

Accordingly, the present invention is directed to a method for obtaining mammalian stem cells which comprises the following steps:

a) harvesting a tissue from a mammalian cadaver stored at 1-6° C., the harvesting being performed on a part of the cadaver's body in which stem cells are usually present in a living counterpart; and b) extracting mononuclear cells from the harvested tissue.

The mammalian cadaver has been stored at 1-6° C., preferably at 3-5° C., and ideally at 4° C. as soon as possible after the death, preferably from 0 minutes to 48 hours after death, and in order of preference from 0 minutes to 24 hours, from 0 minutes to 12 hours and from 0 minutes to 6 hours after death.

More preferably, the cadaver has been stored at 4° C. within 24 hours after death.

The cadaver may be an embryo, a foetus, a neonate, an infant, a child, a juvenile or an adult.

The mammalian cadaver may be a human or a non-human cadaver, e.g. rodent, canine, feline, primate, equine, ovine, bovine, caprine species. According to preferred embodiment of the invention, the mammalian cadaver is a human cadaver.

Tissue harvested up to 30 days after death can be efficiently used to performed the method according to the present invention.

In particular, the tissue harvesting step a) may be performed after a period of time following death comprised between:

0 minute and 30 days, 0 minute and 25 days, 0 minute and 20 days, 0 minute and 15 days, 0 minute and 10 days, or 0 minute and 5 days;

preferably between 20 hours and 30 days, 20 hours and 25 days, 20 hours and 20 days, 20 hours and 15 days, 20 hours and 10 days, or 20 hours and 5 days;

still preferably between 1 day and 30 days, 1 day and 25 days, 1 day and days, 1 day and 15 days, 1 day and 10 days, or 1 day and 5 days;

still preferably between 2 days and 30 days, 2 days and 25 days, 2 days and 20 days, 2 days and 15 days, 2 days and 10 days, or 2 days and 5 days;

still preferably between 3 days and 30 days, 3 days and 25 days, 3 days and 20 days, 3 days and 15 days, 3 days and 10 days, or 3 days and 5 days.

In a preferred embodiment, the temperature of the mammalian cadaver is 1-6° C. before the tissue harvesting step a) is performed.

The longest period of time after which the tissue could not be harvested because it would not contain viable stem cells any more (in part due to tissue decomposition) depends on the mammalian specie and the type of stem cells, and can be easily determined by one of ordinary skill in the art. For instance, for human muscular stem cells, this period of time is comprised between 20 and 30 days.

In the present invention, "death" is intended to mean the moment when the heart of the mammalian definitively stops beating.

The tissue harvested at step a) comes from a part of cadaver's body in which stem cells are usually present in a living counterpart, including central nervous system (brain and spinal cord), bone marrow, peripheral blood, blood vessels, umbilical cord blood, muscle (in particular skeletal muscle or smooth muscle), epidermis of the skin, dental pulp, heart, gut, liver, pancreas, lung, adipose tissue, ovarian epithelium, retina, cornea and testis.

Once the tissue harvested from cadaver, it may be used immediately in step b), or it may be stored before being used in step b) at 1-10° C., preferably at 1-6° C., more preferably at 3-5° C. and still more preferably at 4° C., in normoxia conditions (oxygen concentration of about 21%), preferably in hypoxia conditions (oxygen concentration of less than 5%), and more preferably at an oxygen concentration equal to or of less than 0.1%, preferably in the absence of oxygen. In any case, the harvested tissue should not be stored longer than the maximum period of time after which the tissue does not contain viable stem cells any more. As indicated above, this time period depends on the mammalian species.

The term "extracting mononuclear cells", as use herein, refers to in vitro separation of mononuclear cells from other type of cells present in the harvested tissue. Standard methods to carry out extraction of mononuclear cells are well known by one skilled in the art. For example, one can use the following methods: mechanical dissociation of the tissue (i.e. the tissue is minced into small pieces) followed by enzymatic digestion (using proteolytic enzymes such as pronase, trypsin, dispase, collagenase and/or an association of several enzymes (Chazaud et al., Exp. Cell. Res., 258(2): 237-44, 2000)) and/or or non-enzymatic procedures ($Ca^{2+}$ chelation) and/or an association of mechanical dissociation and enzymatic digestion combined to immunomagnetic cell sorting or FACS-cell sorting (Arnold L, et al., J. Exp. Med., 204(5):1057-69, 2007) and/or association of mechanical dissociation, enzymatic or non-enzymatic digestion followed by Fluorescence-Activated Cell Sorting (FACS) after multiple immunostainings using appropriate markers (for human muscle stem cells CD56+ CD45−). When cells are in suspension such as in blood or in bone marrow, one can use Ficoll Paque plus (Amersham Biosciences) density gradient or adhesion steps (Friedenstein A J, Calci Tissue Int, 56:S17, 1995), as well as immunomagnetic or FACS cell sorting (Prospective isolation of mesenchymal stem cells from multiple mammalian species using cross-reacting anti human monoclonal antibodies).

Antibiotics and antifungus (such as an association of penicillin, streptomycin, gentamycin and amphotericin B) are used to prevent bacterial/fungal contamination of the cell preparation.

The "term mononuclear cell" is intended to mean any cell i) which has a not lobated nucleus, nor multinucleated nucleus, or ii) which has a single nucleus and is preferably able to be dissociated from the tissue and collected in suspension.

In a preferred embodiment, the method comprises an additional step b') following step b) consisting of culturing the extracted mononuclear cells.

Typically, in step b') the extracted mononuclear are cultured for a period of time of 1 day to 30 days, 1 day to 25 days, 1 day to 20 days, 1 day to 15 days, 1 day to 10 days, or 1 day to 5 days, preferably between 2 days to 30 days, 2 days to 25 days, 2 days to 20 days, 2 days to 15 days, 2 days to 10 days, or 2 days to days, still preferably between 3 days to 30 days, 3 days to 25 days, 3 days to days, 3 days to 15 days, 3 days to 10 days, or 3 days to 5 days. For mononuclear extracted from human tissue, culturing step c) is performed preferably for a period of time of 5 to 20 days and more preferably from 7 to 14 days.

Step b') consisting of culturing the mononuclear cells extracted in step b) is conducted at 1-37° C., preferably at 20-37° C., still preferably at 25-37° C., still preferably at 37° C., and at an oxygen concentration equal to or less than 21% and preferably at an oxygen concentration equal to or less than 0.1% to 10%, still preferably from 0 to 5%, still preferably from 0 to 3.5% and more preferably at 3.5%. Preferably, step c) is conducted at a $CO_2$ concentration of 5%.

Culture medium used to perform step b') can be any suitable chemically defined culture medium commonly used for culturing mammalian cells. Such a culture medium is well known to those of ordinary skill in the art. For instance it can be MEM, Dulbecco's Modified Eagle's medium, or modified MEM or DMEM, RPMI 1640 media, CMRL-1066 Medium, Ames' Medium, Ham's F10 and F12 media, Leibovitz's, Williams media Preferably, the culture medium is supplemented with at least one of the growth factors usually used for culturing mammalian cells and which are well known from the skilled person in the art. Suitable growth factors can be selected from the group comprising Fibroblast growth Factors (for instance FGF-1 and FGF-2), Erythropoietin or others colony stimulating factors Epidermal GF (EGF), Insulin (IGF), Stromal GF, Interleukin-1, -3, -6, Flt3-ligand. Growth factors will be selected according to the type of stem cell to be cultured.

Further, feeder cells can be used in step b') to provide nutrients to stem cells and to maintain stem cells in an undifferentiated state. Feeder cells suitable for the cultivation of stem cells are well known from the one skilled in the art and can be chosen from the group comprising the mouse embryonic fibroblasts and human embryonic fibroblasts.

According to an advantageous embodiment of the invention, the culture medium is supplemented with glucose at a final concentration from about 0.5 g/liter to 4.5 g/liter and/or with human or foetal calf serum (or bovine serum substitute) at a final concentration comprised between about 2.5 and 20%. By "about", it is meant that a slightly lower or higher quantity of glucose or serum can be used. When the stem cells obtained by the method subject of the present invention are intended to be introduced in human body, for example in a graft purpose, human or foetal calf serum is replaced by a chemically defined composition (e.i. serum substitute) which acts as sera. Such chemically defined compositions are well known by a person having ordinary skill in the art, and are for example ultroserG™ or platelet lysate (see Bernardo M E, J. Cell. Physiol., 207; 211: 121-130).

In a particular embodiment of the method, step a) is performed on trabecular bone or peripheral blood, the harvested tissue is bone marrow or peripheral blood and the stems cells obtained by the method are hematopoietic stem cells or mesenchymal stem cells.

Peripheral blood is intended to mean circulating blood in a otherwise living mammal, i.e. the cellular components of blood which are found in the vessels or in the arteries and which is not sequestered within the lymphatic system, spleen, liver, or bone marrow.

In another particular embodiment of the method, step a) is performed on muscle, especially skeletal muscle or smooth muscle, the harvested tissue is muscle sample, especially skeletal muscle sample or smooth muscle sample, and the stems cells obtained by the method are muscle stem cells.

In the context of the invention, the term muscular stem cells is intended to mean satellite cells, myogenic precursor cells interstitial muscle or mesenchymal stem cells, preferably obtained from skeletal muscle sample or smooth muscle sample.

In still another particular embodiment of the method, step a) is performed on a nervous tissue such as brain or spinal cord or meninges, preferably at least 24 hours after death, the harvested tissue being brain or spinal cord sample and the stems cells obtained by the method being neural stem cells.

The method according to the invention is suitable for obtaining any types of stem cells, for instance embryonic or foetal stem cells, other adult stem cells such as epithelium stem cells (skin, digestive tract, respiratory tract, oral mucosa, genital mucosa), germ cells, eye stem cells, cancer stem cells.

When the stem cells obtained from a cadaver are intended to be administered to a subject in need thereof, for instance for regenerating an injured tissue, for treating acquired, congenital or genetic disorders (e.g. muscle or neural disorders), for treating malfunction or disease (e.g. hematopoietic system malfunction or disease), the method preferably comprises an ultimate step following step b), or step b') where appropriate, consisting of resuspending the extracted or cultivated mononuclear cells in a pharmaceutically acceptable carrier. The cell suspension thus obtained is suitable for being administered to a subject.

The pharmaceutically acceptable carrier used in this ultimate step should neither be prejudicial for stem cells viability and functions, nor be toxic for a subject in need to be administered with the composition.

Non-limiting examples of pharmaceutically acceptable carriers include saline solution, i.e. a solution having the same osmolarity as blood (e.g. a solution of 0.90% w/v of NaCl, about 300 mOsm/L), Ringer's solution, lactated Ringer's solution, or acetated Ringer's solution.

The obtained mammalian stem cells from cadaver may also be used for preparing transgenic mammalian stem cells expressing a polynucleotide sequence of interest. The invention thus also relates to a method for obtaining mammalian stem cells expressing a transgene of interest, wherein the mononuclear cells extracted from the harvested tissue of step b), or the cultured mononuclear cells of step b') where appropriate, are transformed or transfected with a vector, especially a vector of expression, or transduced with a virus vector, preferably a retrovirus vector, advantageously a lentivirus vector, comprising at least one polynucleotide sequence of interest, so that said at least one polynucleotide sequence of interest is expressed by the mononuclear cells.

In the context of the invention, the term "to transform" means the introduction of a "foreign" (i.e. extrinsic or extracellular) polynucleotide sequence (i.e. gene, portion of a gene, DNA or RNA sequence) of interest into a host cell, so that the host cell will express the introduced gene, portion of a gene, or sequence to produce a desired substance, typically a protein or enzyme encoded by the introduced gene or sequence of interest. The term "to transfect" means the introduction of a foreign nucleic acid into a cell. The term "to transduce with a retrovirus vector" is intended to mean the stable introduction of a "foreign" polynucleotide sequence of interest into the genome of a stem cell by infecting said stem cell with an infectious retrovirus vector whose genome sequence comprises the polynucleotide sequence of interest.

In the context of the invention, the term "Polynucleotide sequence of interest" (also called "transgene") means any gene, portion of a gene, DNA or RNA sequence that is desired to be expressed in the mononuclear cell of step b), or step b') where appropriate. A polynucleotide sequence of interest can be homologous or heterologous to the mononuclear cell genome.

Methods for engineering vectors (viral and non-viral vectors), especially expression vectors, and for transforming, transfecting or transducing mammalian stem cells with a vector, especially a vector of expression, comprising at least one polynucleotide sequence of interest so that said cells express a polynucleotide sequence of interest (called transgenic stem cells) are well known in the art, and are for instance described by Cossu and colleagues (Dellavalle A, Sampaolesi M, Tonlorenzi R, Tagliafico E, Sacchetti B, Perani L, Innocenzi A, Galvez B G, Messina G, Morosetti R, Li S, Belicchi M, Peretti G, Wright W E, Torrente Y, Ferrari S, Bianco P, Cossu G Pericytes of human skeletal muscle are myogenic precursors distinct from satellite cells. Nat Cell Biol. 2007 March; 9(3):255-67. Epub 2007 Feb. 11) or Chamberlain (Li S, Kimura E, Ng R, Fall B M, Meuse L, Reyes M, Faulkner J A, Chamberlain J S. A highly functional mini-dystrophin/GFP fusion gene for cell and gene therapy studies of Duchenne muscular dystrophy. Hum Mol. Genet. 2006 May 15; 15(10):1610-22. Epub 2006 Apr. 4).

When the transgenic stem cells obtained from a cadaver according to the method above recited are intended to be administered to a subject in need thereof, the method preferably comprises an additional step consisting of resuspending the transgenic stem cells in a pharmaceutically acceptable carrier to obtain a composition suitable for being administered to a subject.

The transgene may be any polynucleotide sequence useful for treating a disease.

For instance, when stem cells are muscle stem cells, the transgene may be a polynucleotide sequence encoding dystrophin, calpain, lamin, dysferlin, caveolin, sarcoglycan, myotilin, nemaline, desmin, enzymes such as mitochondrial enzymes, or glycolytic enzymes or growth factors.

Selection of Stem Cells by Exposure to Anoxia

Furthermore, the inventors unexpectedly found that culturing a biological sample comprising stem cells and other cell types in the absence of oxygen triggers death of non-stem cells whereas stem cells survive. Since resistance to anoxia seems to be a general property of stem cells, and because non-stem cells and the great majority of cancer cells do not resist after few hours or few days of anoxia, the inventors took advantage of this property for the enrichment and purification of a biological sample for stem cells.

Consequently, it is another object of the present invention to provide a simple method which leads to the depletion of non-stem cells, such as cancer cells, which may be present and contaminate a harvested tissue, and promotes the enrichment and the purification of stem cells.

In the context of the invention, the term "non-stem cell" is intended to mean any type of cell which is not able to proliferate while maintaining an undifferentiated state and which does not have the capacity to give rise to a succession of mature functional differentiated cells.

The term "cancer cell" is intended to mean a cell which displays uncontrolled growth and which has the capacity to invade adjacent tissues in vivo. This term encompasses cancer cells derived from stem cells.

Accordingly, the invention is also directed to a method for obtaining stem cells comprising the following step:

a) maintaining biological material which usually comprises stem cells at an oxygen concentration equal to or less than 0.1%;

b) selecting viable cells, wherein viable cells are stem cells.

In step a), the biological material is maintained in these conditions during a period of time sufficient to trigger apoptosis and death of non-stem cells without affecting viability of most of the stem cells comprised in the biological material.

According to preferred embodiment of the invention, the biological material is submitted to mechanical dissociation of the tissue (i.e. the tissue is minced into small pieces) followed by enzymatic digestion (using pronase, trypsin, dispase, and/or collagenase or association before carrying out step a) and/or non-enzymatic procedures (Ca2+ chelation) and/or magnetic cell sorting and/or Fluorescence-Activated Cell Sorting (FACS). The period of time necessary to kill non-stem cells without killing stem cells will easily be determined by a person having ordinary skill in the art and will be adapted according to the type of non-stem cells and stem cells present in the biological sample to be treated.

Typically, this period of time is comprised between 12 hours and 60 days,
   preferably between 1 day and 30 days, 1 day and 25 days, 1 day and 20 days, 1 day and 15 days, 1 day and 10 days, or 1 day and 5 days;
   still preferably between 2 days and 30 days, 2 days and 25 days, 2 days and 20 days, 2 days and 15 days, 2 days and 10 days, or 2 days and 5 days;
   still preferably between 3 days and 30 days, 3 days and 25 days, 3 days and 20 days, 3 days and 15 days, 3 days and 10 days, or 3 days and 5 days;
   still preferably between 4 days and 30 days, 4 days and 25 days, 4 days and 20 days, 4 days and 15 days, 4 days and 10 days, or 4 days and 5 days;
   still preferably between 5 days and 30 days, 5 days and 25 days, 5 days and 20 days, 5 days and 15 days, 5 days and 10 days.

Typically, the temperature at which step a) may be performed is comprised between 1-37° C., and in order of preference 1-6° C., 3-5° C., and 4° C.

Preferably, the biological material is maintained at 1-37° C. and at a concentration of less than 0.1% of oxygen for 2 to 20 days.

Step b) is intended to purify stem cells by removing most of dead cells or cell debris from stem cells. This step may be achieved for instance by sorting living stem cells using Fluorescence-Activated Cell Sorting (FACS) and a marker which is specifically expressed by living cells, for instance calcein or by exclusion of dead cells positive for annexin V or propidium iodide, or by using physical separation procedures such as differential centrifugation.

In step a), the biological material is maintained in a culture medium which may be MEM, Dulbecco's Modified Eagle's medium, or modified MEM or DMEM, RPMI 1640 media, CMRL-1066 Medium, Ames' Medium, Ham's F10 and F12 media, Leibovitz's, Williams media.

According to a preferred embodiment of the invention, the method is performed in the absence of oxygen.

In another preferred embodiment of the method, biological material is a cell culture, including cell culture derived from brain, spinal cord, bone marrow, peripheral blood, blood vessels, umbilical cordon blood, muscle (especially skeletal muscle or smooth muscle), epidermis of the skin, dental pulp, heart, gut, liver, pancreas, lung, adipose tissue, ovarian epithelium, retina, cornea and testis.

Preferably, the biological material is a bone marrow or muscular cell culture, especially skeletal muscular cell culture or smooth muscular cell culture.

In a preferred embodiment of the method the biological material is selected from the group consisting of bone marrow and circulating or peripheral blood, and the obtained stem cells are hematopoietic stem cells, peripheral or circulating hematopoietic stem cells or mesenchymal stem cells.

In still a preferred embodiment of the method the biological material is muscle, especially skeletal muscle sample or smooth muscle sample, and the obtained stem cells are muscular stem cells.

In another preferred embodiment of the method the biological material is selected from the group comprising brain, spinal cord and meninges sample, and wherein the enriched stem cells are neural stem cells.

The stem cells obtained by the method of the invention are suitable for being transplanted into a recipient in need thereof.

The biological sample can be obtained from a living donor, except human embryo or foetus, or from a cadaver stored at 1-6° C., preferably at 3-5° C., still preferably at 4° C., directly after death, preferably from 0 minutes to 48 hours after death, and in order of preference from 0 minutes to 24 hours, from 0 minutes to 12 hours and from 0 minutes to 6 hours after death.

The biological sample can be obtained from a human or a non-human donor, e.g. rodent, canine, feline, primate, equine, ovine, bovine, caprine species. According to preferred embodiment of the invention, the mammalian is a human.

The donor may be living or not.

When the stem cells obtained after culture in anoxia (oxygen concentration equal to or less than 0.1%) are intended to be administered to a subject in need thereof, for instance for regenerating an injured tissue, for treating acquired, congenital or genetic disorders (e.g. muscle or neural disorders), for treating malfunction or disease (e.g. hematopoietic system malfunction or disease), the method preferably comprises an ultimate step c) following step b) consisting of resuspending the viable cells of step b) in a pharmaceutically acceptable carrier to obtain a composition suitable for being administered to a subject.

The pharmaceutically acceptable carrier used in this ultimate step should neither be prejudicial for stem cells viability and functions, nor be toxic for a subject in need to be administered with the composition.

Non-limiting examples of pharmaceutically acceptable carriers include saline solution, i.e. a solution having the same osmolarity as blood (e.g. a solution of 0.90% w/v of NaCl, about 300 mOsm/L), Ringer's solution, lactated Ringer's solution, or acetated Ringer's solution.

The method for obtaining mammalian stem cells by exposure to anoxia may also be used for obtaining transgenic mammalian stem cells expressing a polynucleotide sequence of interest (also called "ransgene"). In this method for obtaining mammalian stem cells expressing a gene, or portion of a gene, of interest, the viable cells selected in step b) are transformed, transfected or transduced with a vector, especially a vector of expression, so that at least one polynucleotide sequence of interest is expressed by the mononuclear cells.

When the transgenic stem cells obtained by exposure to anoxia are intended to be administered to a subject in need thereof, the method preferably comprises an additional step consisting of resuspending the transgenic stem cells in a pharmaceutically acceptable carrier to obtain a composition suitable for being administered to a subject.

The transgene may be, for example, any polynucleotide sequence useful for treating a disease.

For instance, when stem cells are muscle stem cells, the transgene may be a polynucleotide sequence encoding the dystrophin, calpain, lamin, dysferlin, caveolin, sarcoglycan, myotilin, nemaline, desmin, enzymes such as mitochondrial enzymes, or glycolytic enzymes or growth factors.

Isolated Muscular Stem Cells

The inventors have found that the expression level of some markers of myogenic cell commitment and of stem-like state are specific of the post mortem derived muscle stem cells.

Therefore, another object of the invention relates to an isolated muscle stem cell characterized in that it does not express myogenin gene (Myogenin⁻).

Preferably, the isolated muscle stem cell of the invention is Pax7$^{high}$ and/or CD34$^+$. The Pax7$^{high}$ level may be determined as a level of expression of Pax7 significantly higher than the level of Pax7 in muscle stem cells isolated from a living subject and in a resting tissue.

Preferably also, the isolated muscle stem cell of the invention has a level of mitochondrial activity (which may be determined by measuring the number of active mitochondria) lower than muscle stem cells isolated from living subject and in a resting tissue).

In an embodiment, the isolated muscle stem cell of the invention is a transgenic cell which expresses a "foreign" polynucleotide of interest (also called "transgene"), as described above.

The transgene may be, for example, any polynucleotide sequence useful for treating a disease or a disorder of muscles.

For instance, when stem cells are muscle stem cells, the transgene may be a polynucleotide sequence encoding dystrophin, calpain, lamin, dysferlin, caveolin, sarcoglycan, myotilin, nemaline, desmin, enzymes such as mitochondrial enzymes, or glycolytic enzymes or growth factors.

In another embodiment, the isolated muscle stem cell or the isolated transgenic muscle stem cell are formulated in a pharmaceutical composition comprising a pharmaceutically acceptable carrier or diluent. Said carrier and diluent should not be prejudicial for stem cells viability and functions and should not be toxic for a subject in need to be administered with the composition. Suitable examples of carriers and diluents have been described above.

Therapeutic Applications

Again another object of the invention relates to method for regenerating an injured tissue, wherein stem cells suitable for regenerating the injured tissue are obtained by any of the methods of the invention disclosed above, and wherein the stem cells are introduced into the body, preferably into the injured tissue, of a patient in need thereof.

The present invention also relates to stem cells obtained or selected by a method of the invention for obtaining stem cells as described above, for use in the regeneration of an injured tissue.

The stem cells may have been transformed to express a transgene.

The stem cells may be introduced into the body parenterally via a vascular vessel (small or large arteries, small or large veins), or introduced directly into the organ comprising the injured tissue.

The injured tissue to be regenerated by the method can be any tissue of the body, including brain, spinal cord, bone marrow, peripheral blood, blood vessels, umbilical cordon blood, muscle (especially skeletal muscle or smooth muscle), epidermis of the skin, dental pulp, heart, gut, liver, pancreas, lung, adipose tissue, ovarian epithelium, retina, cornea and testis.

Preferably, the injured tissue to be regenerated is selected from the group consisting of bone marrow, muscle (especially skeletal muscle or smooth muscle), brain and spinal cord.

When the injured tissue is brain or spinal cord, the stem cells suitable for regenerating the injured tissue are neural stem cells obtained by a method for obtaining stem cells disclosed above.

When the injured tissue is blood tissue or bone marrow, the stem cells suitable for regenerating the injured tissue are hematopoietic stem cells obtained by a method for obtaining stem cells disclosed above.

When the injured tissue is muscle tissue, especially skeletal muscle tissue or smooth muscle tissue, the stem cells suitable for regenerating the injured tissue are muscle stem cells obtained by methods for obtaining stem cells disclosed above. In particular, muscle stem cells may be the Myogenin⁻ stem cells, and preferably Pax7$^{high}$ CD34$^+$, according to the invention.

The invention also relates to a method for treating hematopoietic system malfunction or disease, wherein hematopoietic stem cells obtained by any of the methods of the invention for obtaining or selecting stem cells as recited above are introduced into the body of a patient in need thereof. Preferably, the hematopoietic stem cells are introduced into the vascular system of the patient.

Another object of the invention relates to hematopoietic stem cells obtained or selected by a method as discloses above, for use in the treatment of hematopoietic system malfunction or disease.

The hematopoietic system malfunction or disease to be treated by the method may be selected from the group comprising:

Leukemias and lymphomas, including Acute myelogenous leukemia, Acute lymphoblastic leukemia, Chronic myelogenous leukemia, Chronic lymphocytic leukemia, Juvenile myelomonocytic leukemia, Hodgkin's lymphoma, Non-Hodgkin's lymphoma;

Multiple myeloma and other plasma cell disorders;

Severe aplastic anemia and other marrow failure states, including Severe aplastic anemia, Fanconi anemia, Paroxysmal nocturnal hemoglobinuria (PNH), Pure red cell aplasia, Amegakaryocytosis/congenital thrombocytopenia;

SCID and other inherited immune system disorders, including Severe combined immunodeficiency (SCID, all sub-types), Wiskott-Aldrich syndrome;

Hemoglobinopathies, including Beta thalassemia major, Sickle cell disease;

Hurler's syndrome and other inherited metabolic disorders, including Hurler's syndrome (MPS-IH), Adrenoleukodystrophy, Metachromatic leukodystrophy;

Myelodysplastic and myeloproliferative disorders, including Refractory anemia (all types), Chronic myelomonocytic leukemia, Agnogenic myeloid metaplasia (myelofibrosis);

Familial erythrophagocytic lymphohistiocytosis and other histiocytic disorders.

The invention also relates to method for treating acquired, congenital or genetic muscle disorders, trauma, such as crush or radiation injuries of muscles, or urethral or anal sphincter incompetence (incontinence), or myocardial infarcts, or to increase the muscle mass, for instance for treating a loss of muscle mass in older persons or in persons lain down for a long period of time, wherein muscle stem cells obtained by any of the methods of the invention for obtaining or selecting stem cells as recited above are introduced into the body of a patient in need thereof. Preferably, the muscle stem cells are introduced directly into muscle of the patient in need thereof. In another preferred embodiment, the muscle stem cells are administrated into an artery to obtain a systemic distribution of the stem cells.

The invention also relates to muscle stem cells obtained or selected by a method of the invention as defined above, for use in the treatment of acquired, congenital or genetic muscle disorders, trauma, such as crush or radiation injuries of muscles, or urethral or anal sphincter incompetence (incontinence) or myocardial infarcts.

The acquired, congenital or genetic muscle disorder to be treated is selected from the group comprising:
A) Genetically determined myopathies including
  (i) X-linked muscular dystrophies (Duchenne and Becker);
  (ii) autosomal dystrophies including limb-Girdle muscular dystrophies (such as Miyoshi or distal myopathy, dysferlinopathies, caveolinopathies, sarcoglycanopathies, myotilinopathies), congenital muscular dystrophies, fascio-scapulo-humeral myopathy and oculo-pharyngeal dystrophy;
  (iii) Myotonic dystrophies and non dystrophic myotonias hereditary or not (DM1 or Steinert, DM2 or proximal myotonic myopathies);
B) Congenital myopathies without or with structural anomalies (nemaline myopathy, myo-tubular or centro-nuclear myopathies, central-core or other core disease), for instance Desmin myopathies;
C) Metabolic myopathies including
  (i) Mitochondrial myopathies (such as MELAS, MNGIE, MERRF, . . . );
  (ii) Lipid myopathies;
  (iii) Glycogenosis (such as Mc Ardle disease, pompe disease, Tarui disease).

The invention also relates to a method for treating neural disorders, wherein neural stem cells obtained by any of the methods of the invention for obtaining stem cells as described above are introduced into the body of a patient in need thereof.

The invention also relates to neural stem cells obtained by a method of the invention as disclosed above, for use in the treatment of neural disorders.

In a particular embodiment, the neural disorder to be treated is selected from the group comprising:
A) Neurodegenerative disorders characterized with neuronal loss such as:
  i) dementia or cortical degeneration including Alzheimer's disease, fronto-temporal lobar atrophy, dementia with Lewy Bodies, Pick disease, dementia linked to chromosome 17;
  ii) Movement disorders including Parkinson disease, Progressive supra-nuclear palsy, multiple systeme atrophy, cortico-basal degeneration, Huntington disease, distonias, cerebellar ataxia, hereditary spastic paraparesis;
B) Primary disease of the white matter such as:
  i) Leukodystrophies; and
  ii) white matter disease with inflammation such as multiple sclerosis;
C) Ischemic vascular pathology.

The stem cells used in the above recited method of regeneration of an injured tissue and method of treatment are provided in a pharmaceutically acceptable carrier or diluent which is not prejudicial for stem cells viability and functions not toxic for a subject in need to be administered with the composition. Suitable examples of carriers and diluents have been described above.

Further, the amount of stem cells used in the above recited method of regeneration of an injured tissue and method of treatment is a therapeutically effective amount. A therapeutically effective amount of stem cells is that amount sufficient to achieve tissue repair or regeneration, or to treat or contribute to the treatment of a given disease, malfunction or condition without causing overly negative effects in the subject to which the stem cells are administered. The exact amount of stem cells to be used and the composition to be administered will vary according to the age and the weight of the patient being treated, the type of injury, malfunction or decease, the mode of administration, the frequency of administration as well as the other ingredients in the composition which comprises the stem cells.

Preferably, at least about $1.0 \times 10^5$ cells/kg, at least about $5.0 \times 10^5$, at least about $1.0 \times 10^6$, at least about $5.0 \times 10^6$, at least about $1.0 \times 10^7$, at least about $5.0 \times 10^7$, at least about $1.0 \times 10^8$, at least about $5.0 \times 10^8$, or at least about $1.0 \times 10^9$ cells/kg is used for any treatment. These amounts of stem cells can be delivered to the patient in need thereof in one time or in a sequential way.

Further, it is to be noted that when the disease or the disorders to be treated is not a genetic condition, the administered stem cells can be sourced from the patient (autograft). On the contrary, when the disease or the disorders to be treated is a genetic condition, the patient to be treated can not be the stem cells donor (allograft).

Stem Cell Culture System

The present invention also relates to the use of an anaerobic cell culture system for culturing mammalian stem cells at an oxygen concentration equal to or less than 0.1%, preferably less than 0.1%, and more preferably in the absence of oxygen.

Any known device usually intended to grow anaerobic bacteria is suitable for culturing mammalian. It is preferably totally sterile, i.e. free of any bacteria. Such a device can be a sealed container which achieves an anaerobic environment by chemical reaction, for instance by using a starting chemical material present into the device which reacts with oxygen to deprive the oxygen which is originally contained in the container. It is well understood that the starting chemical products supplied is preferably sterile and must not be toxic for stem cells, and that reaction products must not have detrimental effect on stem cells viability or functions. One can also use a device such as an incubator able to inject N2 instead of oxygen since such a device can also modulate the level of O2 for culture.

Such suitable devices and chemical products are well known by those of ordinary skill in the art, and include Genbag®, Genbox® (biomerieux clinical diagnostic), Gaspak® (BD diagnostic systems), Anaerocult® (vwr international). According to a preferred embodiment of the invention, mammalian stem cells are cultured at 1-6° C., preferably 3-5° C., still preferably at 4° C. for 12 hours to 30 days.

Another object of the invention relates to the use of an anaerobic cell culture system for obtaining (selecting for) stem cells by maintaining in anoxia, i.e. at an oxygen concentration equal to or less than 0.1%, preferably less than 0.1%, and more preferably in the absence of oxygen, a biological sample comprising stem cells and non-stem cells.

The mammalian stem cells may be maintained at 1-37° C. for 2 hours to 30 days 6 hours to 30 days, preferably 12 hours to 30 days and more preferably 24 hours to 30 days.

According to a preferred embodiment of the invention, mammalian stem cells are maintained at 1-6° C., preferably 3-5° C., still preferably at 4° C. for 2 hours to 30 days, 6 hours to 30 days, preferably 12 hours to 30 days and more preferably 24 hours to 30 days.

BRIEF DESCRIPTION OF THE DRAWINGS

The present invention will be further illustrated by the additional description and drawings which follow, which refer to examples illustrating the obtaining of stem cells from cadavers, the enrichment of stem cells by maintaining them at 4° C. in the absence of oxygen and the use of hematopoietic stem cells and muscle stem cells obtained by this method of enrichment for regenerating bone marrow of irradiated mice or skeletal muscle of mice. It should be understood however that these examples are given only by way of illustration of the invention and do not constitute in anyway a limitation thereof.

FIG. 2.B. illustrates the number of viable satellite cells (muscle stem cells) in a sample extracted from the tibialis anterior muscle of Tg:Pax7-nGFP transgenic mouse cadaver (n>5 at each time point). The number of viable satellite cells was evaluated by Flow Cytometry on GFP expression. The number of day after death is shown on the x-axis and the number of GFP positive cells is shown on the y-axis.

FIG. 2.C. illustrates the enrichment of Pax7 expressing satellite cells extracted from the cadaver of knock-in mouse $Pax7^{LacZ/+}$. The enrichment was evaluated by measuring the percentage of X-Gal positive cells. The number of day after death is shown on the x-axis and the number of X-Gal+ cells is shown on the y-axis.

FIG. 2.D. illustrates the proportion of satellite cells that survive after death in a sample extracted from the cadaver of juvenile Tg:Pax7-nGFP transgenic mouse. The juvenile mice in which all SCs are activated have been used. This graph show the absence of decreasing of SCs between day 0 and day 4 post mortem showing that activated SCs can also resist 4 days post mortem. Eight days post mortem very few cells remain alive. Results are expressed as number of cells per mg of tissue. The number of day after death is shown on the x-axis and the number of GFP positive cells is shown on the y-axis.

FIG. 2.E. illustrates the viability of post mortem stem cells in a quiescent cell state Satellite cells were enumerated by FACS from resting or injured TA muscle of Tg:Pax7-nGFP mice at day 0 or 4 days post mortem (pm).

FIG. 3.B. is a graph which illustrates the expression level of markers of myogenic cell commitment, i.e. Troponin, MyoD, Myogenin and, of markers of stem-like state, i.e. Pax7 and CD34 in skeletal muscle sample from mouse cadaver (n=5 mice for each gene). Gene expression was assessed by real time PCR (Taqman). The marker which is quantified is shown on the x-axis and the expression is shown on the y-axis. 2-deltaCT indicates the threshold after which the signal is considered as significant and normalize with ubiquitously expressed gene (TBP: tata binding protein)

FIG. 3.C. illustrates the percentage of clonogenicity of satellite cells (i.e. number of cells forming colonies) after FACS cell sorting and plating in 96 well dishes at day0, 4 and 8 post mortem. The number of day after death is shown on the x-axis and the expression of the percentage clonogenicity is shown on the y-axis.

FIG. 3.D. illustrates the time culture which is necessary to achieve the first division as a function of the number of day following death. The time culture is shown on the y-axis and the number of day after death is shown on the x-axis. This graph shows that cells that remain alive 4 and 8 days post mortem make their first division later than cells collected immediately after death.

FIG. 3.E. illustrates the measurement of the energizing state of satellite cells obtained from Tg:Pax7-nGFP transgenic mouse cadaver as a function of the number of day following death. Comparison was performed between day0, day4 and day8 post mortem. The number of active mitochondria in the different conditions was assessed by Mitotracker. The relative intensity of fluorescence which is the result of the staining of active mitochondria with Mitotracker is shown on the y-axis, and the ratio Day 0/Day X after death is shown on the x-axis.

FIG. 3.F. illustrates the quantity of ATP produced in satellite cells obtained from Tg:Pax7-nGFP transgenic mouse cadaver as a function of the number of day following death. The quantity of ATP was determined by fluorescence using luciferase activity as a readbout. Bioluminescence is shown on the y-axis and the number of day after death is shown on the x-axis.

FIG. 4.A. illustrates the percentage of survival in lethally irradiated mice which have been transplanted with bone marrow extracted from one single femur collected 0, 2, 3 and 4 days post mortem. The number of day after death is shown on the x-axis and percentage of mouse survival is shown on the y-axis.

FIG. 4.B. illustrates the percentage of blood chimerism (% of GFP+ leukocytes in circulating blood) after direct transplantation (black bars) and after a serial transplantation (gray bars) of bone marrow. The number of days after death when bone marrow used for transplantation was harvested is indicated on the x-axis, and percentage of mouse survival is shown on the y-axis. Blood chimerism after bone marrow transplantation using cadaver BM is strictly identical to what observe at day 0 post mortem and decrease lightly when using BM from day 4 post mortem.

FIGS. 4.C-F. illustrate immunophenotyping of circulating GFP+ cells after serial bone marrow transplantation assessed by flow cytometry.

FIG. 4.C shows the percentage of GFP+ B cells (cells expressing B22O cell surface marker).

FIG. 4.D shows the percentage GFP+ T cells (cells expressing CD5 cell surface marker).

FIG. 4.E shows the percentage GFP+ granulocytes (cells expressing Gr1 cell surface marker).

FIG. 4.F shows the percentage and GFP+ myeloid cells (cells expressing CD11b cell surface marker).

These experiments demonstrate the ability of cadaver bone marrow to fully reconstitute blood compartment.

Figure 5:
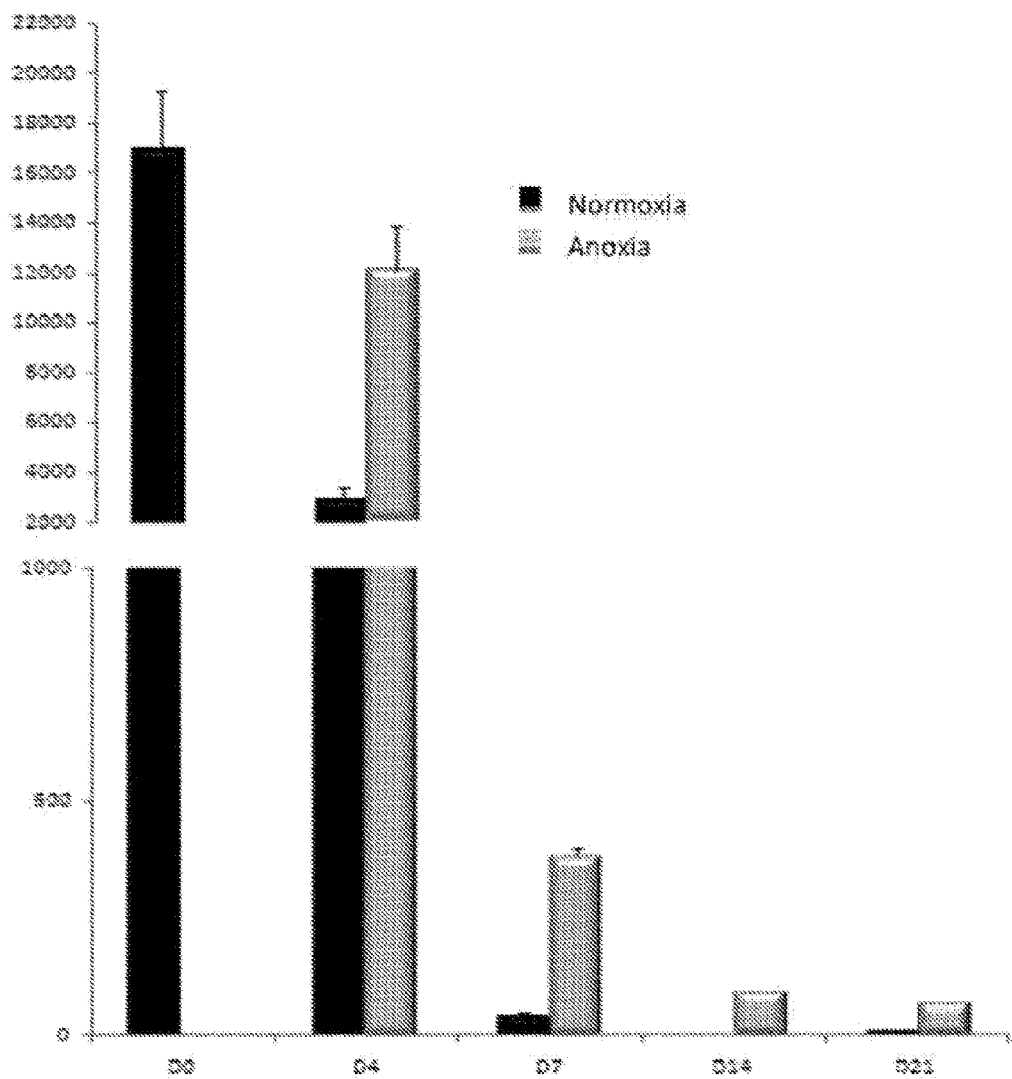

FIG. 5. illustrates the number of cells that remain alive at 4° C. in normoxia (black bars) compared to complete anoxia (gray bars) as a function of days.

FIG. 6.A. illustrates the percentage of whole bone marrow cell loss many days after anoxia at 4° C. (black bars) Four days after storage in anoxia, 95.6% of cells are lost whereas bone marrow is still transplantable at this time point see FIG. 6B.

FIG. 6.B. illustrates the percentage of blood chimerism (% of GFP+ leukocytes in circulating blood) after direct transplantation (black bars) and after a serial transplantation (gray bars) of bone marrow. Transplanted was performed with bone marrow maintain 0 hours, 1 day, 2 days, 3 days or 4 days in anoxia before being transplanted. The number of day in which bone marrow was maintained in anoxia before being transplanted is indicated on the x-axis, and percentage of blood chimerism is shown on the y-axis. Note that n>5 and that 100% of mice survive at each time point.

FIGS. 6.C-F. illustrate immunophenotyping of circulating GFP+ cells after serial bone marrow transplantation assessed by flow cytometry.

FIG. 6.C shows the percentage of GFP+ B cells (cells expressing B22O cell surface marker).

FIG. 6.D shows the percentage GFP+ T cells (cells expressing CD5 cell surface marker).

FIG. 6.E shows the percentage GFP+ granulocytes (cells expressing Gr1 cell surface marker).

FIG. 6.F shows the percentage and GFP+ myeloid cells (cells expressing CD11b cell surface marker).

DETAILED DESCRIPTION OF THE INVENTION

Example I

Material and Methods

Ethical

Human samples were collected according to guidelines recommended by the national ethical committee.

All mice were housed in a level 2 biosafety animal facility, and received food and water ad libitum. Prior to manipulations, animals were anaesthetized using intraperitoneal injection of Ketamine and Xylazine (respectively 25% and 12.5% in PBS). This study was conducted in accordance with the local and EC guidelines for animal care (Journal Officiel des Communautés Européennes, L358, Dec. 18, 1986).

Mouse Strain

C57BL/6 mice (Iffa-Credo, L'arbresle, France), Tg:Pax7-nGFP mice in which satellite cells can be easily visualize by their GFP expression (Sambasivan R, Dev Cell. 2009 June; 16(6):810-21), $Pax7^{nlacZ/+}$ mice in which satellite cells can be easily visualize by their LacZ expression (Ramkumar Sambasivan and Shahragim Tajbakhsh unpublished), Tg:Pax7-nGFP::Tg:CAG:PLAP (Sambasivan 2009) in which all cells constitutively express placental alkaline phosphatise and satellite cell GFP, Tg: CAG-GFP mice (C57BL/6 TgN[actEGFP]Osb YO1) in which the GFP transgene is ubiquitinously expressed under the control of a non-tissue specific promoter, chicken beta-actin with cytomegalovirus enhancer, as a cytoplasmic protein (Okabe, et al, FEBS Lett. 1997 May 5; 407(3):313-9).

Tissue Preparation

Depending of the condition used, after animal sacrifice, tissues were snap-frozen immediately in liquid nitrogen-cooled isopentane for immunohistochemistry and histological analysis, or fixed using buffered 4% paraformaldehyde prior to cryopreservation in 30% sucrose overnight at 4° C. (a procedure that keep the spontaneous fluorescence of GFP in a tissue section). Serial 7 μm thick cryosections were performed for analysis.

Images were captured on a Zeiss Axiophot microscope with an Apotome® (Carl Zeiss Inc., Germany) and Orca ER digital camera (Hamamatsu Photonics, Japan) using Simple PCI (C-Imaging, Compix Inc) software.

Immunohistochemistry

For human cases, 5 μm cryosections of muscles from cadavers were immunostained with mouse anti-human CD56 (1:20 dilution; NHK-1-RD1; Beckman Coulter) and revealed using peroxidase Vectastain ABC kit (Vector Laboratories).

For mouse tissues, immunostainings were done without antigen unmasking. The following protocol was always used: after rehydratation of sections with PBS, non-specific protein binding was blocked with 20% goat serum and cells were permeabilised with 0.5% triton-X100 (Sigma-Aldrich, St-Louis, Mo.) 20 minutes. Incubation with primary antibody was done overnight at 4° C., and signal was revealed with secondary antibody incubated 1 hour at 37° C.

Dako Diluent buffer (Dako, Glostrup, Denmark) was used for diluting antibodies.

The following antibodies were used as primary: mouse monoclonal antibodies against human Placental Alkaline Phosphatase [8B6](1:300, GenTex, Irvine, Calif.), M-cadherin (1:50, Alexis Biochemicals, Lausen, Switzerland), myogenin (1:50, BD Pharmingen, San Jose, Calif.), rabbit polyclonal anti-human (or mouse) desmin (1:50, Abcam, Cambridge, UK), rabbit polyclonal antibodies against mouse myogenin (1:50, Santa Cruz biotechnologies, Santa Cruz, Calif.) and Laminin-1 (1:50, Sigma-Aldrich, Saint-Louis, Mo.).

The secondary antibodies used was Cy3 conjugated donkey anti-mouse (1:400, Jackson Immunoresearch lab., Baltimore, Pa.), FITC conjugated goat anti-mouse (1:200, Jackson), Cy3 conjugated donkey anti-rabbit (1:200, Jackson), biotinilated horse anti-mouse (1:200, Vector laboratories, Burlingame, Calif.), Cy5 conjugated donkey anti-rabbit (1:200, Jackson). FITC conjugated donkey anti-goat (1:200, Jackson) and DTAF conjugated-streptavidin (1:400, Immunotech Beckman, Brea, Calif.).

X-Gal Staining

Cytocentrifuged cells were rehydrated with PBS before fixation with PFA 4% followed by overnight incubation with X-Gal 40 mg/ml (reconstitute in Diméthylsulfoxide, Invitrogen, Paisley, UK) in a solution containing 4 mM each of potassium ferrocyanide, potassium ferricyanide, 2 mM MgCl, and 0.02% NP40 in PBS at 37° C.

Bone Marrow Transplantation

Briefly, donor BM cells were obtained by flushing 2 femurs of donor mice (various times post mortem) with RPMI medium (Invitrogen, Paisley, UK) and 0.1% heparin (Choay 5000 UI/ml). In the case of late post-mortem cadavers the BM cell suspension was incubated with 50 μg/ml DNAse I (Roche, Mannheim, Germany)I to preclude clogging of cells. After washing, retro-orbital injection of cells was done in 0.1 ml fresh mouse serum and Hanks Buffer (PAA Laboratories GmbH, Pasching, Austria) (1:1), in 9.5 Gy-irradiated, 4 week-old B6 mice ($^{60}$Co γ rays within 1 day before BM transplantation). After transplantation, mice received mg/kg/day ciprofloxacin for 10 days to prevent infection during the aplastic phase.

Flow Cytometry Analysis

To quantify the amount of engraftment, the peripheral blood mononuclear cells of transplanted mice were analyzed by flow cytometry using a Cyan™ cytometer (DakoCytomation, Glostrup, Denmark) 1 month post-transplantation. Red blood cells were lysed using "ACK" buffer ($NH_4Cl$ 0.15M, $KHCO_3$ 1 mM, $Na_2EDTA$ 0.1 mM) and immunostainings were done at +4° C. for 30 nm using rat anti mouse CD16/CD32 (Mouse BD Fc Block™) (BD Biosciences) to preclude cell activation and adherence to plastic. In all the FC experiment cells were also labelled with Propidium Iodide 1 mg/ml (Sigma-Aldrich, St-Louis, Mo.) to exclude dead cells from analysis.

Leukocytes were gated on, and GFP fluorescence was measured under the fluorescein isothiocyanate channel. Specific fluorescence stainings were done using PE-Cy5-conjugated anti-Ly-6C (Gr1) (eBioscience San diego, USA). PE-conjugated anti-CD11b (eBioscience San diego, USA), PE-conjugated anti-CD5 (BD Biosciences), PE-conjugated anti-B220 (BD Biosciences), Abs and their respective isotypes. All analyses and quantitation were performed using Summit v4.3 software from DakoCytomation.

For the assessment of active mitochondria immediately after isolation of cells by FACS Mitotracker (invitrogen, M22246) deep red at 500 nM was used for minutes at 37° C. Then the intensity of far red staining was analysed.

ATP Level Measurement

For measuring the levels of ATP, cells were isolated by FACS directly in lysis buffer and maintained at 4° C. An ApoSENSOR™ kit from biovision (Catalog #K254-200, -1000) was used to measure ATP levels where luciferin reacts with ATP and emits signal in proportion to ATP content; emitted light was measured using luminometer (GLOMAX 20/20 luminometer promega).

FACS Cell Sorting and Analysis

MoFlo Legacy (Beckman Coulter, Brea, Calif.) was used for cell sorting and CyAn ADP for cell analysis (Beckman Coulter).

Cell Suspension Preparation from Muscle Tissue

After sacrifice, muscles from mice were carefully dissected, minced in small pieces and washed in PBS before digestion with Pronase (protease from *streptomyces griseus* (Sigma-Aldrich, St-Louis, Mo.) reconstituted in DMEM with penicillin Streptomycin 0.4%). All supernatants were collected and enzyme activity immediately blocked by adding 20% foetal calf serum. This procedure was performed serially until complete digestion of the tissue (4 to 5 rounds of 20 minutes digestion at 37° C.). Cells were then washed and filtered with a 40 μm cell strainer before 10 minutes treatment with an antibiotic/antifungus cocktail.

Cell Cultures

Unless otherwise indicated, culture media components were obtained from GIBCO (Invitrogen, Paisley, UK) and culture plastics were obtained from TPP (Trasadingen, Switzerland). Human or mouse muscle cells were cultured from muscle samples as described previously (Chazaud et al., 2000). In standard conditions (spontaneous in vitro myogenesis), cells were grown in Ham's F12 medium containing 20% FCS (growing medium) 1% UltroserG (PALL Life Sciences, Saint Germain en Laye, France), 0.2% Vitamins, 1% non essentials amino acids 100X, 0.4% Penicillin Streptomycin 10000 U/ml without serum withdrawal. In differentiating conditions, growing medium was replaced by Ham's F12 medium containing 5% FCS (differentiating medium) at time of subconfluence.

For culture without oxygen, GenBag® (Biomerieux, Craponne, France) devices were used.

RNA Extraction, RT and qPCR

Total RNA was extracted from cells isolated by FACS on GFP positivity directly in lysis buffer using the Quiagen RNAeasy Micro purification Kit. 400-600 ng of DNAse-treated (Roche). RNA was processed for random-primed reverse transcripion using the SuperScript II reverse transcriptase protocol of Invitrogen. The cDNAs were then analyzed by real-time PCR using Taqman universal Master Mix and an ABI Prism 7700 (Perkin-Elmer Applied Biosystems) and a StepOnePlus (Applied Biosystems). TBP reference transcript levels were used for the normalisation of each target within each sample (=ΔCT). Custom primers were designed using the Primer3Plus online software.

Statistical Analysis

In all experiments the "n" value was at least 5. The t test was used for statistical analyses (GraphPad-InStat® software). P<0.05 was considered significant.

Example II

Stem Cells Survive for Extended Periods Post Mortem

To determine how long muscle cells would survive in dead tissue, human cadavers were obtained from the "centre du don des corps—Faculté de M-décine Paris Descartes". After death, cadavers were store at 4° after an initial and variable period lasting from several hours to 24 hours at room temperature. In all cases (n=16) patients were from 57-95 y.o. in age (mean 84 y.o.). A deltoid muscle biopsy (2 grams) was performed from 6-17 days post mortem. None of the patients were suffering from neoplasia. Histological analysis of the muscle showed a necrotic appearance and chromatin from myonuclei usually appeared leaky. CD56 immunostaining which labelled satellite cells (SCs) (i.e. muscle tem cells) in human showed a few positive cells were not necrotic, but they exhibited a compact appearance.

Mononuclear cells were extracted from muscle biopsies using standard protocols (Chazaud B, et al. Exp Cell Res. 2000; 258: 237-44.) and cultured for two weeks in gelatin coated dishes and in a "classical" medium composed with HamF12, 20% fetal calf serum, 0.4% penicillin/streptomycin, 1% ultroserG®, 0.2% vitamin, 1% non essential amino-acids. In all cases, including latepost mortem time point (17 days), after a maximum of 4 days, a few cells were observed that were attached to the bottom of the dish. They grew slowly from small colonies and when the density reached a critical threshold, some cells align to fuse. Two weeks post plating, differentiating medium (HamF12, 5% normal horse serum, 0.4% penicillin/streptomycin, 0.2% vitamin, 1% non essential amino-acids) was added to the culture and cell fused forming numerous myotubes.

Immunostainings confirm that more than 90% of the attached cells forming small colonies were expressing the myogenic marker Desmin. This was also the case at later stages when these cells fused and differentiated into myotubes, expressing both Desmin and the differentiation transcription factor Myogenin. Due to the extensive decomposition of tissues, we were not able to obtain cadavers after 17 days post mortem.

To test the survival potential of SCs in muscle samples, we take advantage of organ donors with beating heart in who we perform a surgical muscle biopsy. These Donors were younger in age (n=15; from 41-77 y.o., mean 57 y.o.). We kept the muscle sample in a buffered medium (DMEM, 1 mM HEPES, 0.4% penicillin/streptomycin), at 4° C. in a sealed container. The time of tissue sampling (i.e. number of days between the sampling and the culture) was noted (see Table I below).

TABLE I

| | D2 | D4 | D6 | D10 | D14 | D20 | D25 | D30 | D35 | D40 | D50 | D55 | D60 | D77 |
|---|---|---|---|---|---|---|---|---|---|---|---|---|---|---|
| F 56 y.o. | + | + | + | | | | | | | | | | | |
| F 58 y.o. | + | + | | | | | | | − | − | − | | | |
| F 43 y.o. | | | + | + | | | | | − | − | − | | | |
| M 50 y.o. | | | | | | | | | − | | | | | − |
| F 59 y.o. | + | + | | | | | | | − | | | | | |
| F 57 y.o. | + | + | | | | + | + | | − | − | | | | |
| F 74 y.o. | | | + | | | | | | − | | | | | |
| M 69 y.o. | | | + | | + | + | + | + | | | | | | |
| M 55 y.o. | | | | | | | | | | | | − | − | |
| F 43 y.o. | | | | + | + | + | | − | − | | | | | |
| M 65 y.o. | | | | + | | | + | − | | − | | | | |
| M 54 y.o. | | | | | | | | | − | | | | | |
| M 55 y.o. | | | | | | + | + | − | | | | | | |
| F 41 y.o | | | | | | | | | − | | | | | |
| F 77 y.o | | | | | + | | + | | − | | | | | |

As observed in cadavers, and from day 4 post-biopsy, muscle exhibited a necrotic appearance with some remaining CD56 immunopositive and other compact small cells adjacent to myofibers. Depending of the size of the sample, culturing muscle cells was possible many days after sampling. The samples were assayed regularly from day 2-77. Prior to day 30 post-sampling, the majority of cells, the majority (>80%) being myogenic as assessed by the formation of myotubes that expressed Myogenin and Desmin. After 35 days post-sampling viable cells were no longer obtained (assayed for 15 days in culture).

Figure 1:
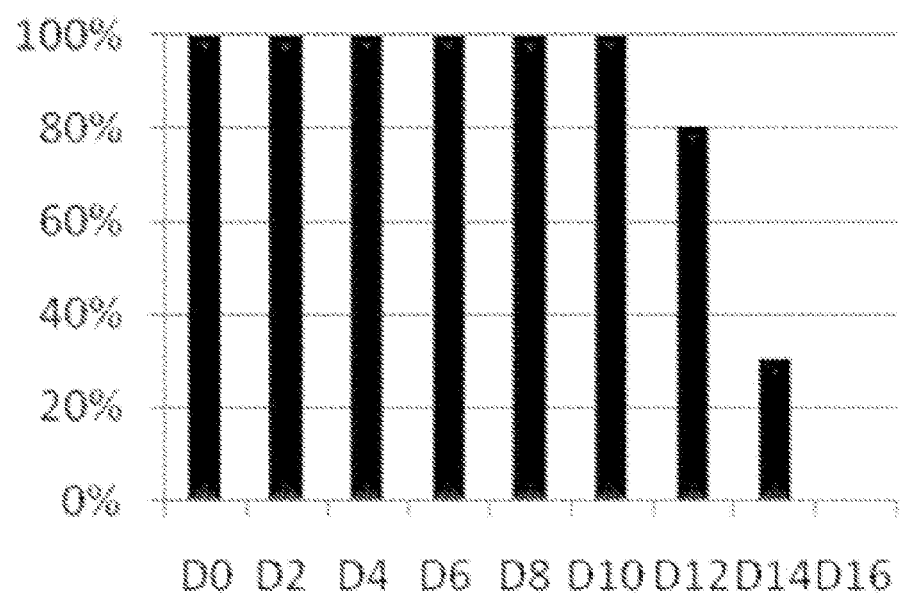
FIG. 1 illustrates the percentage of animals giving rise to myogenic cultures (after 14 days in culture) every 4 days after death. N=10 at each time point.
Figure 2A:
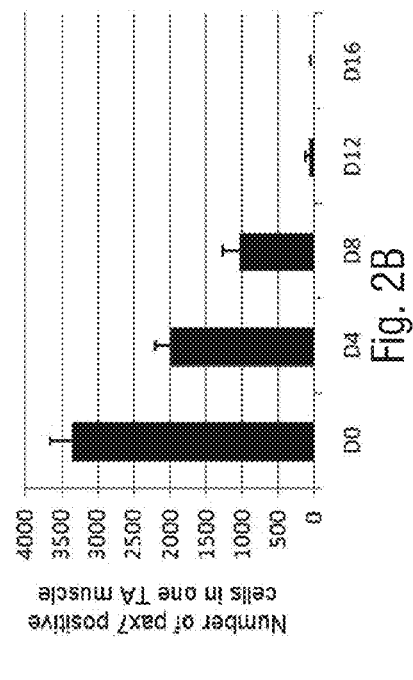
FIG. 2.A. illustrates the number of viable stem cells extracted from one mg of muscle of mouse cadaver up to 8 days after death. The number of viable cells was evaluated by Flow Cytometry on calcein incorporation and propidium iodide exclusion (n>5 at each time point). The number of day after death is shown on the x-axis and the number of cells labelled with calcein is shown on the y-axis. This figure shows a linear decreasing of cells alive in muscle tissue after 4 and 8 days after death.
Figure 2B:
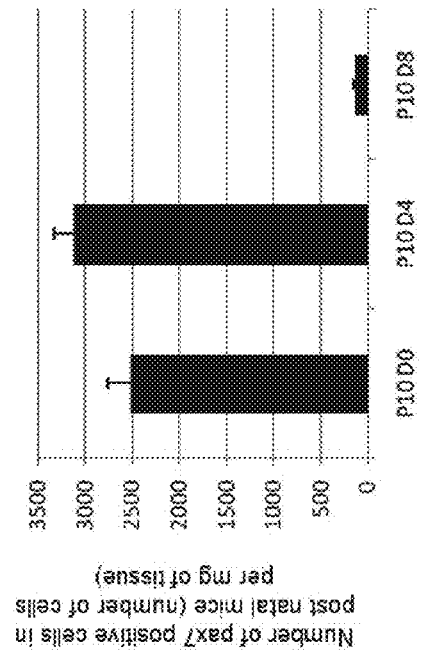
Figure 2C:
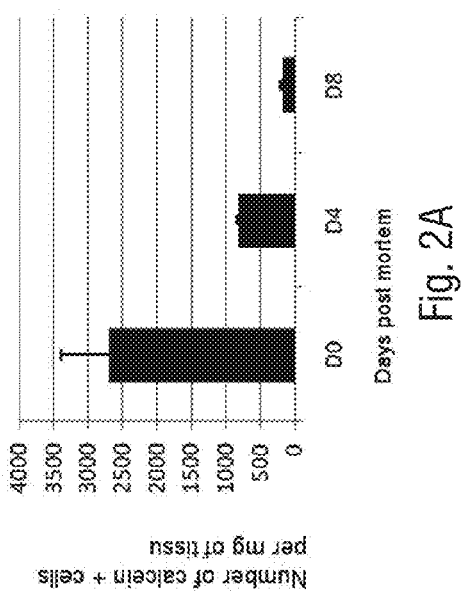
Figure 2D:
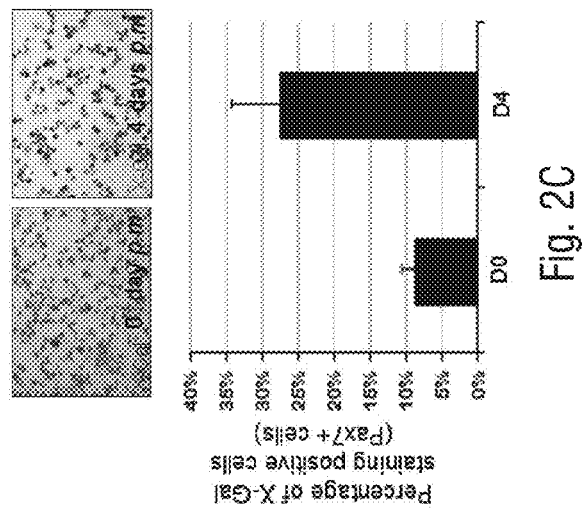
Figure 2E:
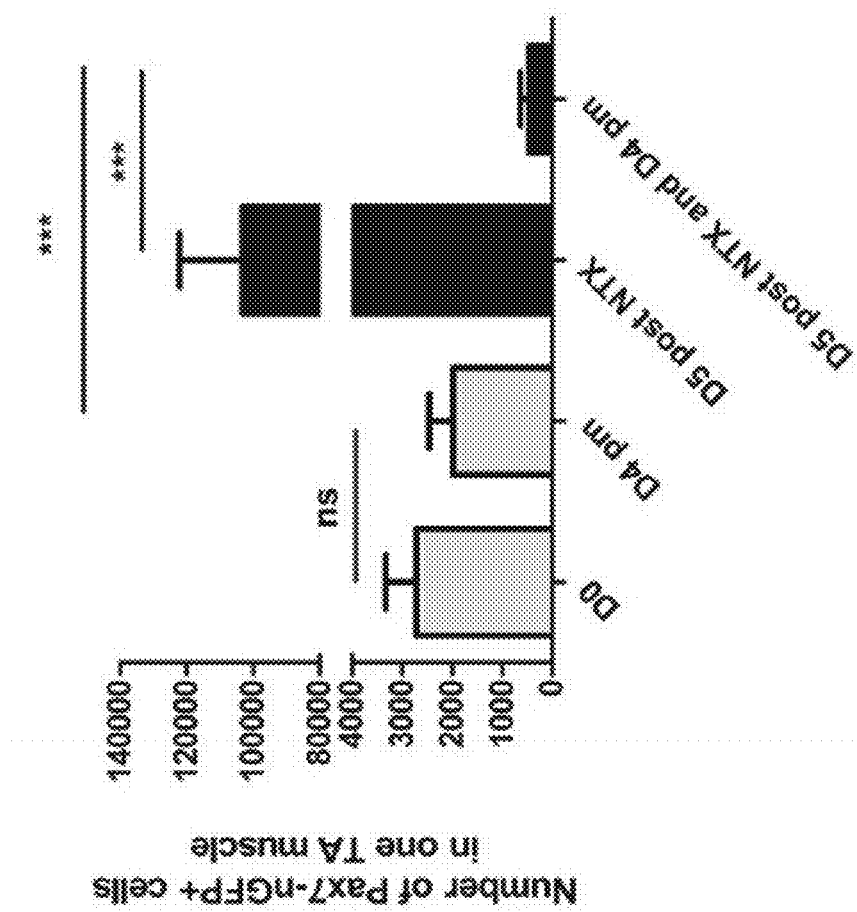

Similar results were obtained with mouse cadavers. C57BL6 mice (n=10 per time point) were sacrificed using $CO_2$ and kept for several days at 4° C. (FIG. 1). Skeletal muscles displayed a necrotic and oedematous appearance with some remaining M-cadherin expressing cells a marker for SCs. Muscle SCs were cultured up to 10 days after isolation. One hundred percent (n=10) of the cases gave rise to a large number of SCs. After 10 days post mortem, most of the cases did not yield viable cells in culture, in part because of the contamination of the medium by bacteria arising during tissue decomposition. Mouse cadavers were more sensitive to bacterial proliferation (even at 4° C.) than humans. Up to ten days post mortem, all cultured cells were myogenic as assessed by the formation of myotubes and the expression of myogenic markers.

Example III

Characterisation of Cell Types that Survive after Organismal Death

To determine if stem cells have a greater capacity to survive after organismal death, cell suspensions obtained from cadavers were stained with calcein that labels only live cells and evaluated the number of cells that remained alive by flow cytometry (FC). As shown in FIG. 2.A. the number of cells incorporating calcein per mg of tissue (n=7 animals at each time point) varies from 2678±718 at day 0 to 820±33 at day 4 and 179±22 at day 8 post mortem.

To determine the number of viable SCs in a tissue after organism death, the Tg:Pax7nGFP mice were used in order to take advantage that all their satellite cells are GFP-positive and that SCs could be prospectively isolated by FACS based on GFP epifluorescence (Sambasivan R, Dev Cell. 2009 June; 16(6):810-21). The number of SCs in one Tibialis anterior (TA) muscle was enumerated every four days after death from 8 week old mice kept at 4° C. As shown in FIG. 2.B. four days after death, 50% of SCs remained in the TA. Eight days after death, 30% of the SCs survived in the TA. By 12 or 16 days post mortem only a few viable SCs remained (2% and 1%, respectively). All GFP+ cells isolated by FACS were viable as assayed by the exclusion of propidium iodide, and the ability to give colonies when cultured.

To determine the proportion of SCs that survive after death, the knock-in mouse $Pax7^{nlacZ/+}$ was used. In this mouse, bacterial lacZ reporter gene expression reflects the expression of the Pax7 gene in all satellite cells (R. Sambasian and S. Tajbakhsh, unpublished). Between day 0 and day 4 post mortem, the proportion of X-gal positive cells increased by 3.4 fold (see FIG. 2.C.) indicating that a higher proportion of muscle stem cells were present after organismal death.

To investigate the mechanism that permits muscle stem cells to survive after organismal death, it was examined whether cellular quiescence conferred a survival advantage compared to proliferating cells. To do this, we counted SCs from Tg:Pax7-nGFP in juvenile mice before SCs entered quiescence (growth paradigm). At P10 (10 days postnatal), satellite cells proliferate actively and myofibres continue to increase in size due to the addition of nascent myoblasts (Shinin V, et al. Nat Cell Biol. 2006 July; 8(7):677-687; White R B, et al. BMC Dev Biol. 2010 22; 10:21). In this scenario, no significant drop in SCs number between day 0 and day 4 post mortem (FIG. 2.D.) was observed after sacrifice of the pups. However, dramatic decrease was observer after 8 days post mortem.

To confirm that quiescent state might confer a survival advantage to the stem cells, three cohorts of mice were examined. In the first, satellite cells were enumerated from uninjured TA muscle of Tg:Pax7-nGFP mice at 4 days post mortem (1980±212 GFP$^+$/TA; n=5 mice; see FIG. 2.E). Satellite cells in the second cohort were enumerated 5 days after a severe muscle injury with a myotoxin, thereby promoting stem cell re-entry into the cell cycle to effect myofibre regeneration. At this time, myogenic cells proliferate actively (mean 103,000±8494 GFP$^+$/TA; n=5 mice; see FIG. 2.E). The third cohort was treated similarly, but 5 days post-injury, mice were sacrificed, then satellite cells were isolated by FACS at 4 days post mortem (mean 460±80 GFP$^+$/TA, n=5 mice). Therefore, the majority of proliferating myogenic cells do not survive in post mortem tissue suggesting that cellular quiescence, in part, protects stem cells from death in post mortem tissue.

Example IV

Characterisation of Viable Cells after Organismal Death

Figure 3B:
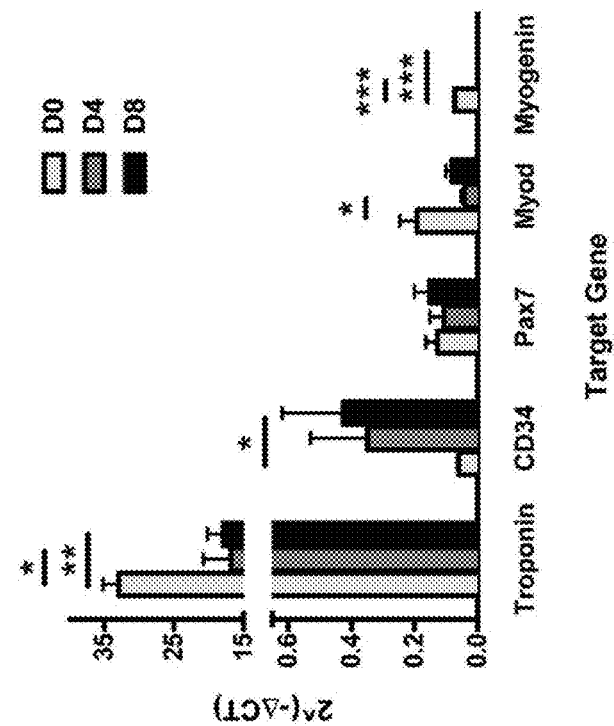
FIG. 3.A. is a graph which illustrates the expression level of two satellite cell key genes, i.e. Pax7 and MyoD, in skeletal muscle sample from mouse cadaver (n=5 at each time point). Gene expression was assessed by real time PCR (Taqman). The number of day after death is shown on the x-axis and the expression of Pax7 and MyoD is shown on the y-axis. 2-deltaCT indicates the threshold after which the signal is considered as significant and normalize with ubiquitously expressed gene (GAPDH: Glyceraldehyde 3-phosphate dehydrogenase).
Figure 3A:
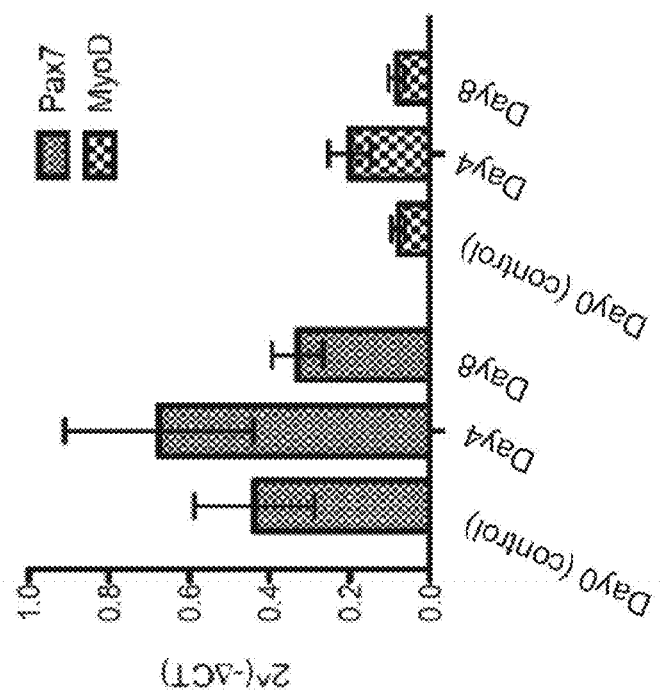

To characterise the surviving SCs sub-population after death in mouse skeletal muscle, RT-qPCR were performed on purified satellite cells isolated by FACS and lysed directly in buffer. A library of cDNA was synthesized by reverse transcription and real time PCR (Taqman) was performed to assess the gene expression level of key satellite cell genes. The level of Pax7 and MyoD were similar in surviving cells day 4 and day 8 post mortem vs. cells extracted immediately after death (n=5) (FIG. 3.A.). Complementary experiments were carried out to further assess the extent of lineage priming and hence, the commitment status of the muscle stem cells post mortem. To do that, we performed RT-qPCR on purified satellite cells isolated by FACS. Cell determination and differentiation markers Myod and Myogenin, and the myofibre structural protein Troponin T were used as readouts for myogenic cell commitment whereas Pax7 and the receptor stem cell marker CD34 were used as readouts of the more stem-like state. Interestingly, a progressive increase in the levels of CD34 was observed from day 0 to day 8 post mortem, whereas an inverse trend was noted for MyoD, Myogenin and Troponin T transcript levels (n=5 mice/condition; see FIG. 3.B). This suggests that the post mortem derived muscle stem cells are less transcriptionally primed for myogenic commitment compared to those isolated from freshly isolated tissue.

Further, these data clearly show that the post mortem derived muscle stem cells are characterized by a lack of detectable expression of Myogenin gene, while muscle stem cells extracted immediately after death (which is considered as representing cells present in a living subject) do express myogenin.

To assess the functional potential of surviving satellite cells, clonal analysis of cells sorted from Tg:Pax7-nGFP mice was performed. The percentage of clonogenicity (i.e. percentage of cell forming colonies after FACS in a 96 well plate) was not significantly different between day 0 and day 4 post mortem (20% vs. 16.3%) but this value drops dramatically at day 8 post mortem (1.6%) (FIG. 3.C.). This suggests strongly that satellite cells are able to resist to stress from the environment after organismal death. All colonies were myogenic as assessed by contracting myotube formation after differentiation. Although potential to form colonies was equivalent between day 0 and day 4 post mortem, we observed that exit from cell quiescence, assessed by scoring the first division after plating, was longer in post mortem (29 hours) sorted cells in comparison to alive animals (21 hours) (see FIG. 3.D.). After the first division cells divided every 7 hours and synchronously in the tested culture conditions in both situations indicating that cells recovered their correct cell cycle time after culture from dead animals.

To characterize further the sub-population of resisting cells in a hostile environment, their energizing state was measured by assessing the mitochondrial number and activity, as well as ATP level in SCs 4 days post mortem. To do this, SCs were isolated by FACS from Tg:Pax7-nGFP mice from day 0, day 4 and day 8 animals post mortem. Staining with Mitotracker allowed assessing the number of active mitochondria in the different conditions by flow cytometry. The number of active mitochondria was significantly diminished in post mortem samples compared to live control adult animals. Interestingly, as shown in FIG. 3.E., no significant difference in this value was observed between day 4 and 8 post mortem. The level of ATP in the 3 conditions was also monitored (alive—day 0—, day 4 and 8 post mortem). Cells were isolated as indicated above. For all 3 conditions, 20,000 cells were used and this number was double-checked by direct counting with a Malassez Chamber®. The quantity of ATP was determined by fluorescence using luciferase activity as readout. Like mitochondrial activity, the quantity of ATP dropped dramatically in day 4 and day 8 post mortem in comparison to the day 0 "alive" controls (FIG. 3.F.).

Taken together these results reveal a direct correlation between the energizing threshold of the cell, presumably to ensure essential basal cellular activity and maintain viablilty, and the capacity to resist to a hostile environment. Cells exhibiting values below this threshold are not viable. These readouts provide insights into the mechanisms that allow these stem cells to survive after organismal death, and they provide a powerful tool to be used in diagnostic and therapeutical purposes.

To determine if stem cells have the functional capacity to regenerate a tissue after transplantation, SCs were extracted 4 days post mortem and engrafted into preinjured regenerating skeletal muscles of immunocompromised Rag1/2$^{-/-}$:C$^{-/-}$ recipient mice. Donor mice were double transgenic Tg:Pax7-nGFP::Tg:CAG-PLAP (PLAP, human alkaline phosphatase) mice to prospectively isolate satellite cells by FACS using GFP. The ubiquitous reporter PLAP permits to follow the fate of the engrafted cells.

In all the cases a significant contribution to regenerating skeletal muscle by the donor population was observed. After engrafting 10,000 SCs extracted from day 4 post-mortem mice, a mean of 300 PLAP-expressing myofibers were obtained. This result is similar to what is observed using control freshly isolated satellite cells.

Example V

Assessment of the Viability and Engraftment Potential of Haematopoietic Stem Cells Isolated from Mice Post Mortem To determine if this extreme resistance to post mortem conditions is only the case for skeletal muscle stem cells, or another stem cell population behaves in a similar manner, hematopoietic stem cells were studied. At daily intervals post mortem, the bone marrow (BM) of Tg:CAG-GFP mouse femur was flushed (two limbs) and kept at 4° C. BM transplantations were performed in lethally irradiated C57BL6 recipient mice. The engraftment potential of transplanted BM progenitors was assessed by the percentage of GFP+ leukocytes found in the circulating blood. Using, 2, 3 and 4 days post mortem BM, blood cells were readily and fully reconstituted by BM progenitors in lethally irradiated recipients (n>5 in each case). Viability was ensured with all the animals that received a BM transplantation except when using BM from 4 days post mortem where viability was 60% (FIG. 4.A.). In all these animals GFP+ cells represented more than 70% of leukocytes, a result normally found in controls (donors) corresponding to 100% chimerism (FIG. 4.B.) After serial transplantation, same results were obtained except at day 4 where only 50% chimerism was found. In all these experiments 100% of animals survive. In all the cases, GFP+ leukocytes were found in all lineages: lymphocytes B, lymphocytes T, granulocytes, or monocytes as assessed by flow cytometry using B220, CD5, Gr1 or CD11b expression, respectively (FIGS. 4.C. to 4.F.).

To determine if the cells that were extracted from post mortem BM contained long term hematopoietic stem cells, a serial transplantation was performed with the grafted BM. GFP+ cells from the bone marrow of previously grafted animals were isolated by FACS 2 months after the first transplantation and re-grafted in lethally irradiated recipients. In all the cases, independently of the source of the initial BM (day 2, 3 or 4 post mortem), all of the animals were viable with 100% chimerism, and we obtained GFP+ leukocytes in all the different lineages.

Example VI

Anoxia and Low Temperature Enhance the Viability and Transplantation Potential of Stem Cells Isolated Post Mortem To investigate the mechanism which confers the observed resistance of stem cells, the hostile environment occurring after death in a tissue i.e. hypoxia followed by anoxia was modeled. Culture conditions was established with a device usually used to culturing anaerobic bacteria (GenBag Chambers®). The cells were maintained at 4° C. for various time intervals in the absence oxygen (less than 0.1% according to manufacturer). SCs isolated by FACS from Tg:Pax7-nGFP mice were maintained at 4° C. for 4, 7, 14 and 21 days in the absence oxygen (less than 0.1% according to manufacturer). Strikingly, it was observed that SCs better survived in a complete anoxic environment than in normoxic (20%) environment at 4° C. (see FIG. 5). As an example, after 4 days at 4° C., 82.3% of SCs were lost in the normoxia condition compared to 28.9% in anoxia and after 7 days at 4° C., 99.7% of cells were lost in normoxia compared to 97.7% in anoxia (FIG. 5.). The functional capacity of these cells was maintained after several days without oxygen as assessed by their ability to grow and differentiate when cultured under normal conditions. To test the functional capacity of these cells in greater detail, SCs from Tg:Pax7-nGFP::Tg:CAG-PLAP donor mice were isolated by FACS and maintained at 4° C. with or without oxygen until 4 days days. After this period, the cells were transplanted them by intramuscular injection into pre-injured TA muscles of C57BL6 recipient mice. These results demonstrate that cells maintained without oxygen had at least the same transplantation capacity than those maintained with oxygen.

Similar experiments were performed with hematopoietic stem cells isolated from mice post mortem and stored in the presence or absence of oxygen. BM cells were extracted from two femurs of Tg:CAG-GFP animals, kept at 4° C. for 1, 2, 3, or 4 days, and transplanted into lethally irradiated C57BL6 recipient mice (n≥5). Cell mortality in such conditions was important i.e. 63+/−7% of cell loss compare to immediately after extraction after one day in anoxia, 79+/−3% after two days in anoxia, 98+/−1 after 3 days in anoxia and 96+/−1 after 4 days in anoxia (FIG. 6A). Even with this important cell loss, number of cells was sufficient enough to graft into irradiated recipients and blood chimerism was slightly 100% (FIG. 6.B. black bars) and all hematopoietic lineages were reconstituted (FIGS. 6.C. to 6.F.). Serial transplantations of BM cells isolated after the first round of transplantation demonstrated that the HSCs had a long term capacity repopulate the lineage (FIG. 6.B. grey bars).

In summary, the inventors have shown in animal model that transplantation of skeletal muscle and hematopoietic stem cells obtained from cadavers by the method of the invention, or enriched from biological sample when maintained in the absence of oxygen are functional and contribute to the regeneration of their respective tissues.

The invention claimed is:

1. A method of obtaining skeletal muscle stem cells comprising the following steps:
    a) maintaining a biological sample at an oxygen concentration equal to or less than 0.1% and at a temperature of 1-6° C. during a period of time of at least 2 days wherein the biological material is a skeletal muscle sample; and
    b) selecting the viable cells, wherein viable cells are skeletal muscle cells.

2. A method of obtaining mammalian skeletal muscle stem cells expressing a transgene of interest, comprising the following steps:
    a) maintaining a biological material at an oxygen concentration equal to or less than 0.1% and at a temperature of 1-6° C. during a period of time of at least 2 days, wherein the biological material is a skeletal muscle sample;
    b) selecting viable cells, wherein viable cells are skeletal muscle stem cells;
    c) transforming or transfecting the viable skeletal muscle stem cells.

3. The method according to claim 1, wherein the biological material is obtained from a living donor, except human embryo or foetus.

4. The method according to claim 1, wherein the biological material is maintained at 1-6° C. during a period of time of 2 days to 60 days.

5. The method according to claim 1, wherein the biological material is maintained at 1-6° C. in the absence of oxygen.

6. The method according claim 1, wherein the biological material was obtained from a mammal cadaver stored at 1-6° C. within 48 hours after death.

7. The method according to claim 3, wherein the biological material is obtained from a living mammal.

8. The method according to claim 1, further comprising an ultimate step following step b) consisting of resuspending the selected viable skeletal muscle stem cells in a pharmaceutically acceptable carrier.

9. A method for selecting skeletal muscle stem cells comprising using an anaerobic cell culture system for selecting stem cells by maintaining a skeletal muscle sample comprising stem cells and non-stem cells at an oxygen concentration equal to or less than 0.1% and at a temperature of 1-6° C. during a period of time of at least 2 days.

10. The method according to claim 2, further comprising an ultimate step following step c) consisting of resuspending the selected viable skeletal muscle stem cells in a pharmaceutically acceptable carrier.

11. The method according to claim 1, wherein the skeletal muscle sample is maintained at an oxygen concentration equal to or less than 0.1% and at a temperature of 1-6° C. during a period of time of at least 4 days.

12. The method according to claim 2, wherein the skeletal muscle sample is maintained at an oxygen concentration equal to or less than 0.1% and at a temperature of 1-6° C. during a period of time of at least 4 days.

13. The method according to claim 9, wherein the skeletal muscle sample is maintained at an oxygen concentration equal to or less than 0.1% and at a temperature of 1-6° C. during a period of time of at least 4 day.

* * * * *